US012605156B2

(12) United States Patent
Khristov et al.

(10) Patent No.: US 12,605,156 B2
(45) Date of Patent: Apr. 21, 2026

(54) TISSUE CLAMP AND IMPLANTATION METHOD

(71) Applicant: The United States of America, as represented by the Secretary, Department of Health and Human Services, Bethesda, MD (US)

(72) Inventors: Vladimir R. Khristov, Washington, DC (US); Steven T. Charles, Memphis, TN (US); Juan A. Amaral, Silver Spring, MD (US); Arvydas Maminishkis, Washington, DC (US); Kapil Bharti, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 204 days.

(21) Appl. No.: 18/226,043

(22) Filed: Jul. 25, 2023

(65) Prior Publication Data

US 2024/0115261 A1     Apr. 11, 2024

Related U.S. Application Data

(62) Division of application No. 16/348,855, filed as application No. PCT/US2017/060672 on Nov. 8, 2017, now Pat. No. 11,717,298.

(Continued)

(51) Int. Cl.
*A61B 17/08*          (2006.01)
*A61B 17/04*          (2006.01)
(52) U.S. Cl.
CPC ........ *A61B 17/083* (2013.01); *A61B 17/0482* (2013.01); *A61B 2017/081* (2013.01)

(58) Field of Classification Search
None
See application file for complete search history.

(56) References Cited

U.S. PATENT DOCUMENTS

| | | | |
|---|---|---|---|
| 1,123,290 A | 1/1915 | Herff | |
| 2,215,725 A | 9/1940 | Andres | |

(Continued)

FOREIGN PATENT DOCUMENTS

| | | | |
|---|---|---|---|
| EP | 2 889 374 A1 | 7/2015 | |
| WO | WO 2012/177968 A1 | 12/2012 | |

(Continued)

OTHER PUBLICATIONS

Chen et al., "Layer-by-Layer Bioprinting of Stem Cells for Retinal Tissue Regeneration," University of California, San Diego, 14 pages (Dec. 1, 2016).

(Continued)

*Primary Examiner* — Shaun L David
(74) *Attorney, Agent, or Firm* — Leydig, Voit & Mayer, Ltd.

(57)               ABSTRACT

A surgical clamp for aligning the margins of incised or wounded tissue has jaws with parallel clamping faces, and a handle for manipulating the clamp to align the margins of the tissue. The jaws are in a normally closed position, however they can be opened by compressing the handle to open the jaws. Prongs project from the inferior surface of the jaws. The clamp is positioned in a desired position over the margins of a wound to be closed, the prongs engage the margins of the wound to be aligned, and the jaws are closed by releasing compressive force on the handle. As the jaws close the prongs help move the tissue into alignment. Suture guide slots through the jaws assist in the placement of precisely placed sutures across the incision. The disclosed surgical clamp is particularly suited for selectively closing and reopening surgical incisions, such as a sclerotomy (Continued)

incision in the eye. Methods are disclosed for using the clamp during intraocular and other surgical or minimally invasive procedures. In one example the clamp is used during implantation into the retina of a scaffold on which choroid and retinal pigment epithelium cells and retina grow in a three-dimensional matrix that mimics the native structure of the retina.

26 Claims, 15 Drawing Sheets

Related U.S. Application Data

(60) Provisional application No. 62/419,804, filed on Nov. 9, 2016.

(56) References Cited

U.S. PATENT DOCUMENTS

| | | | |
|---|---|---|---|
| 3,586,002 A | | 6/1971 | Wood |
| 3,868,957 A | | 3/1975 | Doddington |
| 4,112,951 A | | 9/1978 | Hulka et al. |
| 4,146,130 A | | 3/1979 | Samuels et al. |
| 4,269,190 A | | 5/1981 | Behney |
| 4,327,450 A | * | 5/1982 | Girard ..................... A61F 2/16 |
| | | | 128/898 |
| 4,444,187 A | | 4/1984 | Perlin |
| 4,449,530 A | | 5/1984 | Bendel et al. |
| 4,765,335 A | * | 8/1988 | Schmidt ............. A61B 17/1227 |
| | | | 24/552 |
| 4,799,481 A | | 1/1989 | Transue et al. |
| 4,844,066 A | | 7/1989 | Stein |
| 4,957,500 A | | 9/1990 | Liang et al. |
| 4,976,722 A | | 12/1990 | Failla |
| 5,053,045 A | | 10/1991 | Schmidt et al. |
| 5,201,746 A | | 4/1993 | Shichman |
| 5,366,458 A | | 11/1994 | Korthoff et al. |
| 5,534,008 A | | 7/1996 | Acksel |
| 5,593,414 A | | 1/1997 | Shipp et al. |
| 5,601,574 A | | 2/1997 | Stefanchik et al. |
| 5,695,505 A | | 12/1997 | Yoon |
| 6,179,850 B1 | | 1/2001 | Goradia et al. |
| 6,217,594 B1 | | 4/2001 | Hallen et al. |
| 9,220,507 B1 | | 12/2015 | Patel et al. |
| 2003/0236550 A1 | | 12/2003 | Peterson et al. |
| 2004/0133218 A1 | * | 7/2004 | Charles ................ A61B 17/083 |
| | | | 606/151 |
| 2005/0251204 A1 | | 11/2005 | Attinger et al. |
| 2011/0004304 A1 | | 1/2011 | Tao et al. |
| 2013/0004469 A1 | | 1/2013 | Glazier et al. |
| 2013/0149284 A1 | * | 6/2013 | Malcuit ................ C12N 5/0621 |
| | | | 435/377 |
| 2013/0204294 A1 | | 8/2013 | Filips et al. |
| 2016/0122723 A1 | | 5/2016 | Retting et al. |

FOREIGN PATENT DOCUMENTS

| | | | |
|---|---|---|---|
| WO | WO 2014/121077 A2 | 8/2014 | |
| WO | WO 2016/007852 A1 | 1/2016 | |
| WO | WO 2016/049345 A1 | 3/2016 | |
| WO | WO 2017/044483 A1 | 3/2017 | |
| WO | WO 2018/089521 A1 | 5/2018 | |
| WO | WO 2018/144515 A1 | 8/2018 | |

OTHER PUBLICATIONS

International Search Report and Written Opinion mailed in International Application No. PCT/US2017/060672, mailed on Mar. 26, 2018, 13 pages.
EP Office Action for related Application No. 17801272.0, 9 pages, mailed Jun. 9, 2021.

* cited by examiner

Retina

Pupil

Lens

Iris

FIG. 13E

Retina

Pupil

Lens

Iris

FIG. 13F

TISSUE CLAMP AND IMPLANTATION METHOD

CROSS REFERENCE TO RELATED APPLICATIONS

This is a divisional application of U.S. application Ser. No. 16/348,855 filed May 9, 2019, which is a U.S. National Stage of International Application No. PCT/US2017060672 filed Nov. 8, 2017, which was published in English under PCT Article 21(2), which in turn claims the benefit of U.S. Provisional Application 62/419,804 filed Nov. 9, 2016, each of which is incorporated herein in its entirety.

STATEMENT OF GOVERNMENT SUPPORT

This invention was made with government support under project no. Z01 #: EY000533-03 awarded by the National Institutes of Health, the National Eye Institute. The government has certain rights in the invention.

FIELD

The invention relates to surgical tissue clamps and methods of using them, as well as transplantation techniques.

BACKGROUND

Minimally invasive surgery has reduced surgical tissue damage by permitting procedures to be performed with miniaturized instruments introduced through smaller incisions. However, minimally invasive procedures often require multiple small incisions through which different instruments are introduced into the body. For example, minimally invasive surgery may require introducing cutters, cannulas, and illuminated laser probes into the body through the various incisions.

During vitreoretinal surgery multiple instruments are introduced through scleral openings (sclerotomies) in the wall of the eye through which vitreous humor and other fluids can leak. Loss of intraocular fluids can lead to surgical complications, such as collapse of the eye, retinal bleeding, and detachment of the retina. Some intra-intraocular procedures, such as retinal transplantation or implantation with in vitro retinal tissue, may require making unusually large incisions in that eye that must be repeatedly opened and closed without while minimizing disruption of the pressure equilibrium within the eye. Fluid-tight scleral incisions would avoid excessive or continuous fluid loss that necessitates constant infusion of replacement fluid into the eye.

Many other surgical or traumatic wounds require selective closure with apposition of aligned edges (margins) of the wound. Examples of such wounds include an incision in a large blood vessel, the skin, or in a hollow viscus (such as the bowel). Battlefield or other traumatic injuries may cause wounds such as lacerations that require prompt closure to achieve life-saving hemostasis or penetrating injuries that may require temporary closure pending full surgical repair.

Currently available medical clamps do not readily reversibly join opposing edges of surgical incisions in a secure and efficient manner to maintain structural integrity of incisions of varying sizes. Incisions may be manually sutured to close the wound and the sutures then removed to open it, but this approach is time-consuming and may damage the tissue. U.S. Pat. No. 6,217,594 discloses an elongated malleable metal clamp that is crimped on the surface of the eye to create scleral folds and close incisions. U.S. Patent Publication 2005/0251204 describes a wound clamp having hinged identical halves that are biased together with springs or an elastic band to clamp underlying tissue. Each half of the wound clamp has a cut out portion that in association with the other half of the clamp leaves a central aperture in the clamp when it is closed. U.S. Patent Publication 2013/0204294 shows a clam shell clamp having complementary opposing arms with distal ends that can be locked in place with a ratchet to quickly close surgical and traumatic wounds.

Surgical clips are commonly used to ligate, clamp or otherwise occlude blood vessels in a surgical site to maintain the surgical site relatively free of blood and minimize blood loss. The clips are often in the form of thin, narrow, metal or polymeric U-shaped or V-shaped members that are placed over the vessel or tissue and then forced into a closed position using a clip applicator. The clips, typically constructed of metal, may be initially open and then permanently deformed into a closed or clamped configuration around the desired blood vessel or other tissue structure using an appropriate clip applicator. Examples of such clips are described in U.S. Pat. Nos. 5,201,746; 4,976,722; 4,844,066; 4,799,481; 4,449,530; and 4,146,130.

Clips that have clamping members formed in a normally closed position are also known. Normally closed clips typically have their clamping members biased together by way of the elasticity of the material from which it is constructed. In general, to apply a clip configured in a normally closed position, the clamping members must be forced open by an appropriate clip applicator and then released to its closed position in place over the desired structure to be clamped. Normally closed clips may be formed of a continuous wire having a torsion spring or tension coil as described, for example, in U.S. Pat. No. 5,593,414 or it may be of a variety of other configurations such as, for example, those described in U.S. Pat. Nos. 5,695,505; 5,601,574; 5,366,458; and 4,957,500.

There is a need for a convenient tissue clamp that can be easily manually manipulated to selectively open and close surgical incisions and traumatic wounds, such as penetrating injuries that must be quickly closed to achieve hemostasis and protect the wound until surgical repair can be completed.

SUMMARY

The foregoing need is addressed by the disclosed surgical instrument for clamping a target structure, such as the edges of a surgical incision or other wound. The instrument has a clamp with a first jaw forming a first clamping surface, and a second jaw forming a second clamping surface that opposes the first clamping surface. A handle connects the first and second jaws wherein the handle has a resilient bias that biases the first clamping surface and second clamping surface against each other into a substantially closed relationship for clamping the target structure. The handle functions like a normally-closed clip that is movable to overcome the resilient bias and open the clamp by moving the first jaw and/or the second jaw to an open position while maintaining the first clamping surface and the second clamping surface in a substantially parallel orientation relative to one another.

In some examples, the handle is a clip-like structure made of a single continuous length of resiliently biased material configured to open the jaws in response to a compressive force applied to the handle. The handle may be a continuous metal or alloy wire connector that has an arm portion and a leg portion that may be co-planar with one another. The arm portion has first and second substantially parallel arms that are respectively connected to the first jaw and the second jaw, while the legs are non-parallel and join at a common apex of the leg portion with a resilient bias that closes the jaws. Compression of the non-parallel legs of the handle moves the first and second arms against the resilient bias to open the jaws. In some embodiments, at an intermediate portion of the handle (between the arm and leg portions), the handle crosses over itself, for example to form a stabilization channel. Compression of the leg portion moves the first and second arms and attached jaws away from each other without twisting of the jaws out of a predetermined (for example parallel) relationship. Compression of the handle of the instrument permits the jaws to be opened with dexterity by a surgeon or assistant during a procedure. This ease of use allows the wound to be repeatedly closed and reopened during the course of the procedure if required, for example to introduce and remove instruments from the body while selectively securely closing the wound when open access is not required. In some embodiments the jaws of the clamps do not form an opening through which surgical instruments other than a needle may be placed. Alternatively a small aperture may be provided through the closed jaws forming a surgical port channel to access the eye cavity without opening the clamp. Some surgical instruments, such as retino-vitreal instruments (for example a 25 or 27 gauge retinal forceps or vitreous cutter) may be introduced through the aperture of the closed jaws into the eye.

In some embodiments, the handle is compressible to open the clamp while maintaining the first and second clamping surfaces in a substantially parallel relationship to one another. An alignment guide maintains the first and second clamping surfaces in the substantially parallel relationship to one another to resist torque as the jaws open and close. For example, the alignment guide may be interdigitating alignment members carried respectively by each of the first and second jaws. In an illustrated embodiment, the alignment members include a pair of parallel guide bars extending from the first jaw toward the second jaw, and an alignment bar extending from the second jaw toward the first jaw. The alignment bar slides between the parallel guide bars to maintain movement of the jaws in a plane defined by the parallel guide bars. In other embodiments the alignment guide is a channel on the handle, for example formed by bending the wire frame of the handle into an alignment channel through which one of the arms of the instrument projects to guide movement of that arm in the plane defined by the plane of the guide channel.

In some embodiments, a suture guide slot extends through the first and second jaws to define a needle trajectory for placing a suture across an incision that is closed by the clamp. For example, the suture guide slot extends transversely between the first and second jaws a predetermined distance that corresponds to the entrance and exit points of a suture placed across the incision. The guide slot may have a bevel at its ends (opposite ends of the slot) to guide a needle along the needle trajectory. The guide slot helps control the width and depth of the suture, which can be particularly advantageous when operating on relatively thin structures such as the wall of the eye.

In yet other embodiments, the clamp has an inferior surface cooperatively formed by the first and second jaws for resting on tissue to be clamped, and an opposing superior surface cooperatively formed by the first and second jaws, and the clamp thickness tapers toward the clamping faces and the suture guide slot to minimize clamp thickness along the path of the suture guide. One or both of the superior and inferior surfaces may be arcuate. An arcuate superior surface may, for example, narrow the thickness of the jaws toward the clamping faces and the suture guide slot. In other examples, the superior surface is arcuate and tapers symmetrically with respect to the opposing clamping faces, and the suture guide slot extends substantially perpendicularly to the opposing clamping faces. In other examples, the inferior surface of the jaws is curved to conform to the shape of a target structure, such as an anatomic structure to be clamped, for example the wall of a bowel, a blood vessel, or the wall of an eye. In yet other embodiments the jaws are narrow curved members having top and bottom surfaces that are curved at a predetermined radius of curvature that conforms to a shape of an underlying surface to be clamped. For example, when the clamp is to be used on a curved surface such as the eye the radius of curvature could be about 10-14 mm, for example 12 mm.

In other embodiments, compression prongs extend downwardly from the inferior surface of each jaw and toward each other and the incision to be closed. The prongs may be substantially straight needles or curved barbs, although straight needle barbs can provide improved hemostasis at the margins of the wound.

Methods are also disclosed for using the clamp to close a wound. The clamp may be opened by moving the handle, for example by compressing the handle to overcome the normally closed bias of the jaws. The clamp is placed on the wound with the margins of the wound between the clamping surfaces of the jaws, and the clamp is closed with the margins of the wound retained between the clamping surfaces. The wound may be sutured with the clamp in place on the wound, for example by introducing a needle and suture into the guide slot along a trajectory defined by the slot in the jaws. In those embodiments that have barbs on the jaws, the barbs grab tissue on opposing edges of the wound. Although the wound may be the result of traumatic injury, the clamp is particularly adapted to use in surgical procedures for selectively closing and opening a surgical incision. In particular examples it is used for intraocular surgery, such as vitreoretinal procedures, for selectively opening and closing an incision to help maintain intraocular fluid balance and avoid unwanted complications such as collapse of the eye, hemorrhage, and retinal detachment.

Emerging potential cell-based therapies in the eye that have been devised to treat age-related macular degeneration (AMD), geographic atrophy (GA), RPE tears, choroidal neovascularization, and retinitis pigmentosa (RP) require delivery of newly grown sheets of cells, such as the retinal pigment epithelium (RPE), retinal cells, choroidal cells, microvessel, or a combination thereof. A retinal prosthesis electrode chip may also be used, for example the Argus® II artificial retina. Many of these procedures are performed through a large sclerotomy in order to deliver tissue to the inside of the eye, which pose an increased risk of eye collapse, retinal detachments, and bleeding due to loss of intraocular pressure (IOP). These risks can be minimized by use of the presently disclosed clamp that can be maintained closed when not in use, and allows repeated re-entry through the wound. For example, the clamp can be used in a procedure to deliver iPS cell-derived RPE cell sheets grown on a biodegradable scaffold into the subretinal space. In other disclosed examples, the clamp is useful for rapid closure of a penetrating traumatic injury to the eye, or surgery on any anatomic structure, such as a body cavity, blood vessel or hollow viscus.

When used on the eye, the clamp can close large eye wounds to maintain and/or stabilize intraocular pressure. In eye or any other type of surgery the clamp can also help establish hemostasis. The clamp can provide exact tissue alignment, and in some embodiments even permits precise suture placement at a controlled depth and distance from the tissue edge. It allows for the passage of surgical instruments into the eye, and can be scaled and modified to apply to a variety of surgical procedures. The disclosed clamp permits opposing margins of the wound to be precisely and selectively aligned and, readily reopened to permit re-entry through the sclerotomy, and subsequently aligned for superior permanent closure with sutures.

The foregoing and other objects, features, and advantages of the invention will become more apparent from the following detailed description, which proceeds with reference to the accompanying figures.

BRIEF DESCRIPTION OF THE DRAWINGS

FIGS. 13A through 13H schematically illustrate a surgical procedure for delivering a subretinal implant into the eye through a scleral incision that may be selectively opened and closed with the surgical clamp. The eye is prepared for surgery using a standard three or four port vitrectomy procedure. FIG. 13A shows the retina separated from the retinal pigment epithelium by injecting saline solution under the retina. FIG. 13B shows an implant entry port created by making an incision in the retina within the area of retinal separation. In FIG. 13C an incision is made through the sclera, and one of the disclosed surgical clamps is applied to the scleral incision site to maintain intraocular pressure during the procedure. In FIG. 13D the clamp is temporarily opened or removed and a tissue transplantation tool is inserted into the subretinal space through the previously created retinal incision. In FIG. 13E the implant is deposited in the subretinal space, and in FIG. 13F the implantation tool is retracted and the clamp is re-applied to the scleral incision. In some embodiments the clamp includes suture guides to facilitate placement of sutures of an appropriate depth and/or distance from one another to securely close the incision.

FIGS. 14A and 14B shows a tubular transplantation device for introducing transplanted cells into the eye (such as into the retina); the jaws of the clamp are slightly opened to accommodate the diameter of the transplantation device (which is greater than the diameter of the aperture). FIGS. 14C and 14D show a smaller diameter vitrectomy device that is of a sufficiently small diameter to be placed directly through the small aperture in the jaws and into the eye during a surgical procedure on the eye.

DETAILED DESCRIPTION

As used herein, the singular forms "a", and "the" include plural forms unless the context clearly dictates otherwise. Unless specifically stated or obvious from context, as used herein, the term "or" is understood to be inclusive. The term "including" is used herein to mean, and is used interchangeably with, the phrase "including but not limited to." The terms "comprises," "comprising," "containing," "having" and the like can have the meaning ascribed to them in U.S. Patent law and can mean "includes," "including," and the like; "consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Distal" and "proximal" are used with reference to the user of the instrument. Hence a "proximal" portion of the instrument is closer in use to the operator, and a "distal" portion is farther from the operator in use. For example, the handle of the disclosed instrument is proximal and the jaws are more distal to the person using the instrument to clamp the incision.

"Retinal transplantation" refers to delivery of retinal tissue grants through a sclerotomy. The retinal tissue graft may be actual retinal tissue, artificial retinal tissue, component parts of the retina, or scaffolds on Which retinal cells can grow.

The term "subject" or "patient" refers to an animal which is the object of treatment, observation, or experiment. By way of example only, a subject includes, but is not limited to, a mammal, including, but not limited to, a human or a non-human mammal, such as a nom human primate, murine, bovine, equine, canine, ovine, or feline.

A "sclerotomy" is a surgical incision made through the wall of the eye, for example to expose the anterior chamber or posterior chamber of the eye.

"Vitreoretinal surgery" refers to procedures performed on the vitreous and/or retina of the eye. A "vitrectomy" is a controlled surgical approach typically performed with an operating microscope and a vitrectomy machine, which is a hand-held cutting and aspirating instrument connected to a console that can be selectively activated by an operator. An intraocular cutting/aspirating tip has a hollow movable inner shaft, and variable negative pressure can be applied through the shaft. There is a small port at the distal end of the shaft, and a the hollow inner shaft moves the outer port opens and closes to pull in vitreous tissue as negative pressure is applied. The vitrectomy system further includes a light source and an infusion line, through which an infusion solution is introduced to maintain a normal pressure-volume relationship intraoperatively.

Figure 1:
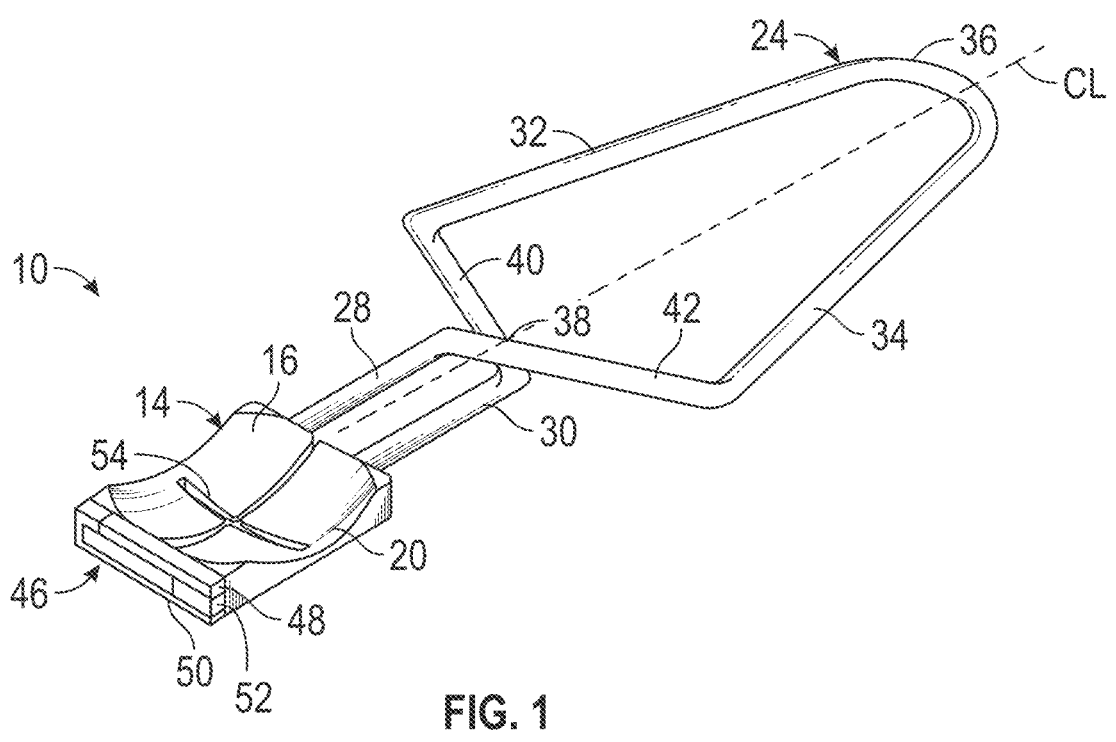
FIG. 1 is top perspective view of a first embodiment of the surgical clamp in a closed configuration in which the opposing inner faces of the clamp jaws appose to close an incision or other wound.
Figure 2:
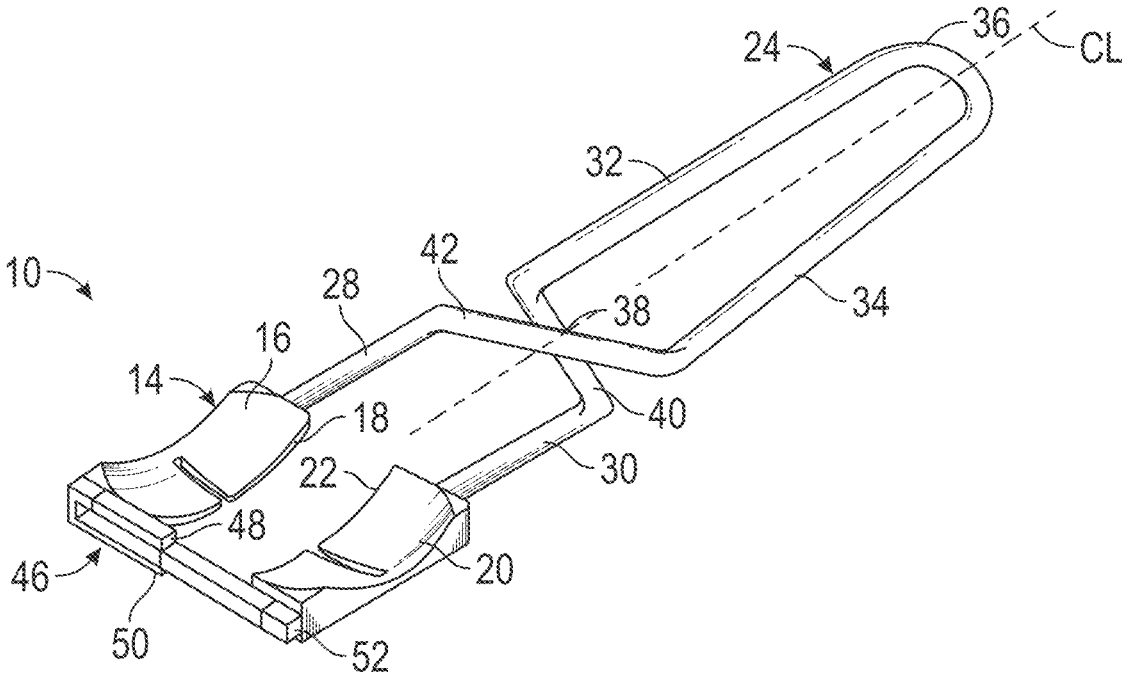
FIG. 2 is a top perspective view of the clamp shown in FIG. 1 but with the spring clip handle compressed to open the jaws of the clamp body.
Figure 5:
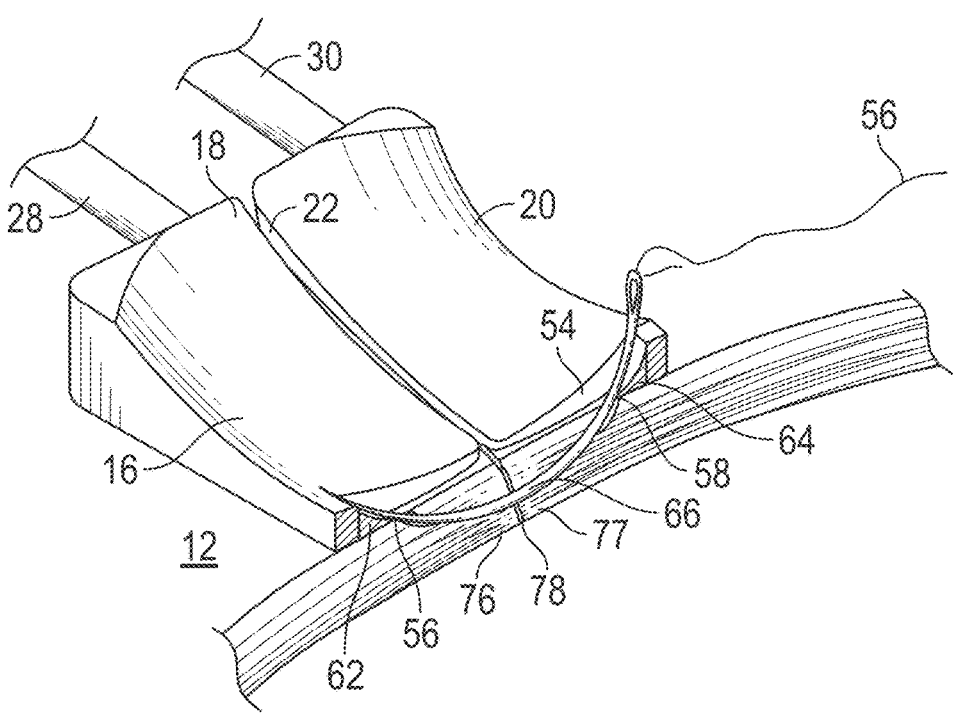
FIG. 5 is an isolated perspective view, partially in section, of a portion of the clamp taken along lines 5-5 in FIG. 4 through the needle guide of the clamp jaws.
Figure 6:
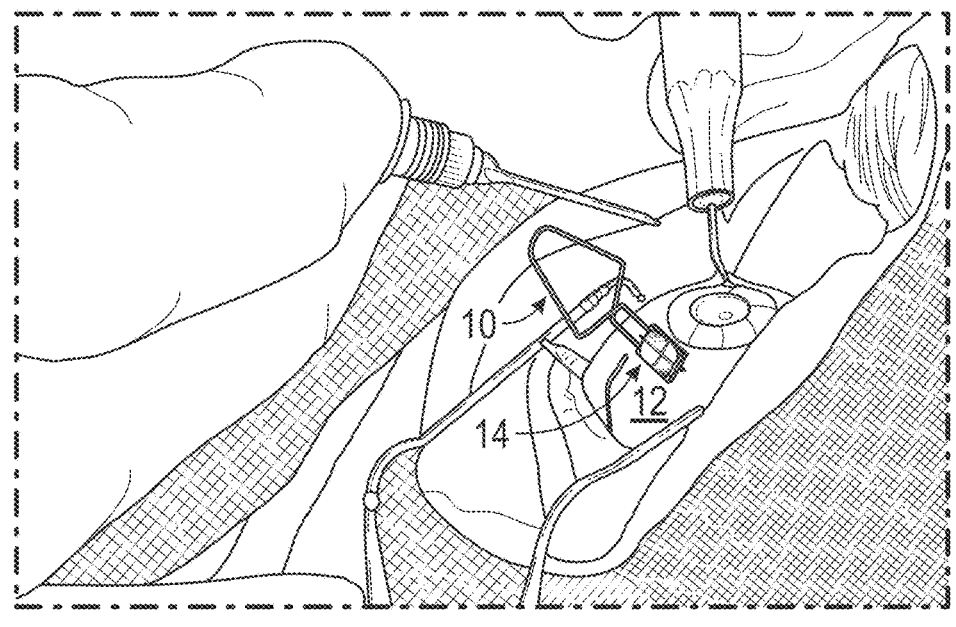
FIG. 6 is a schematic view of the surgical clamp in use to close a sclerotomy incision in the eye of a patient during a vitreoretinal surgical procedure.

FIGS. 1-6 illustrate a first embodiment of a surgical instrument 10 for clamping a target structure 12, for example an anatomic target structure such as the eye (FIG. 6). Clamp 12 includes a first jaw 16 forming a first narrow planar clamping surface 18, and a second jaw 20 forming second narrow planar clamping surface 22 (FIG. 2). The illustrated clamping surfaces 18, 22 are narrow flat mirror image faces of jaws 16, 20 that are maintained substantially parallel to one another by the instrument. A handle 24 connects first and second jaws 16, 20 and has a resilient bias that biases the first and second clamping surfaces 18, 22 against each other into a substantially closed relationship for clamping a target structure (such as the opposing margins of a surgical incision) between clamping surfaces 18, 22. Handle 24 is movable to overcome the resilient bias and open the clamp by moving jaws 16, 20 to an open position while maintaining clamping surfaces 18, 22 in a substantially parallel orientation relative to one another. The clamp illustrated in FIGS. 1-5 has rectangular-shaped mirror image jaws of the substantially the same widths, but the jaws can also be of different widths and not mirror images of one another. The jaws may meet along a centerline CL of the instrument and be symmetric with respect to one another, for example when the first and second jaws are of substantially the same dimensions and mirror images of one another.

Handle 24 provides a means for a user to grasp instrument 10 and manipulate it with one hand to open and close clamp 14 by manipulating the handle with the same hand that holds it. For example, in FIGS. 1 and 2 the handle is a single continuous length of resiliently biased wire frame material configured to open jaws 16, 20 in response to a compressive force applied to the handle. The material is a single continuous non-slip treated bendable wire that is formed or bent to form an arm portion connected to jaws 16, 18 and a leg portion that would be more proximal to the user. The ends of the wire form first and second substantially parallel arms 28, 30 that are respectively connected to the first and second jaws 16, 18. The leg portion is a continuous loop formed by non-parallel legs 32, 34 that are joined at a common distal apex 36 of the leg portion and have a resilient bias that closes the jaws. For purposes of illustration, a centerline CL of the instrument is shown that bisects handle 24 symmetrically.

In the illustrated example of the normally closed instrument shown in FIG. 1, an intermediate portion 38 of the handle crosses over itself at the centerline of the instrument, where the leg portion meets the arm portion, such that movement of legs 32, 34 toward one another against the bias of the legs increases the distance between arms 28, 30. In FIG. 1 the biased handle is not compressed, and legs 32, 34 extend away from one another at an angle from common apex 36 such that the distance between legs 32, 34 (and from centerline CL) increases as they move from the apex toward intermediate portion 38. However, terminal segments 40, 42 respectively of legs 32, 34 incline toward the centerline CL and cross one another at intermediate portion 38 and centerline CL. After crossing, each of terminal segments 40, 42 then bend again toward a parallel alignment to form substantially parallel arms 30, 28 respectively.

Hence the continuous handle in the non-biased condition shown in FIG. 1 includes first arm 28 that extends parallel to centerline CL then bends toward centerline CL (for example at an angle of about 45 degrees) into terminal segment 42, which extends across centerline CL at intermediate portion 38. The continuous wire of the handle then bends at an angle that is greater than the angle at which arms 28 are bent, but back toward the centerline CL, such that leg 34 inclines toward apex 36 where it meets leg 32. Leg 32 then continues from apex 36, away from centerline CL until its terminal segment 40 bends toward centerline CL and crosses under terminal segment 42 before it bends again to a parallel relationship with centerline CL to form arm 30. The illustrated handle 24 is therefore compressible to open the jaws of the clamp while maintaining first and second clamping surfaces 18, 20 substantially parallel to one another.

Parallel alignment of clamping surfaces 18, 20 is assisted by an alignment guide 46 that resists torque in the instrument as the handle is compressed. The alignment guide can take many forms in which mating portions of first and second jaws 16, 18 interdigitate during all or a portion of the movement of jaws 16, 18 to maintain them in alignment and resist torque that would otherwise interfere with the ability of the clamp to close securely with clamping surfaces 18, 20 in secure abutment. An example of the alignment guide is illustrated in FIGS. 1-4, and it includes interdigitating alignment members carried respectively by each of first and second jaws 16, 20 at their distal ends. A pair of parallel guide bars 48, 50 are carried by first jaw 16 at its distal end and extend toward an alignment bar 52 projecting along the distal edge of second jaw 20 toward guide bars 48, 50. Alignment bar 52 slides between guide bars 48, 50 as jaws 16, 18 move toward and away from one another to stabilize the jaws relative to one another and maintain them in a common plane as clamp 14 is opened and closed.

During use of clamp 14, once the margins of an incision or other wound have been temporarily brought into apposition by closing the clamp, the wound may be more securely or permanently closed by placing sutures across the margins of the incisions. Placement of precise sutures of an appropriate depth and width is facilitated by a suture guide slot that extends through first and second jaws 16, 18 to define a needle trajectory for placing a suture 56 across the wound. Guide slot 54 extends transversely across first and second jaws 18 a predetermined distance that corresponds to the distance between entrance point 58 and exit point 60 (FIG. 5) of suture 56 placed across the incision. In the illustrated example, guide slot 54 has a bevel 62, 64 at its ends to support a curved suture needle in its trajectory into and out of the slot, and through the tissue underneath the clamp.

Jaws 16, 18 depicted in FIGS. 1-2 are generally rectangular members that are elongated in a longitudinal direction along centerline CL of clamp 14 with jaws 16, 18 extending longitudinally away from arms 28, 30 to which they are connected. The clamp therefore has two outside longitudinal edges that are substantially parallel to clamping surfaces 18, 22, and two transverse edges that are substantially perpendicular to the longitudinal edges. The jaws each have an inferior face that cooperatively form an inferior face of clamp 14 for resting on tissue of target structure 12 to be clamped (FIGS. 5 and 6). Jaws 16, 18 also each have an opposite, superior face cooperatively forming a superior surface of the clamp.

As illustrated in FIGS. 1-2 and 4-5, the thickness of clamp 14 tapers toward clamping surfaces 18, 22 and transverse guide slot 54 to facilitate placement of the suture through the guide slot. The thickness of clamp 14 is therefore at its minimum (thinnest) in the center of the clamp at the intersection of clamping surfaces 18, 22 and guide slot 54. Bevels 62, 64 (FIG. 5) at each end of guide slot 54 have a curved upper surface that slopes at an angle from the inferior surface to the superior surface of clamp 14 at a radius of curvature that complements the trajectory of a curved needle that is used to place suture 56 in the clamped tissue 12. In the illustrated embodiment, the superior surface of clamp 14 is arcuate and tapers symmetrically with respect to clamping surfaces 18, 22 and guide slot 54 such that clamp 14 is thickest along its outer margins, for example at its opposing longitudinal edges, and along its opposing transverse edges. Arms 28, 30 connect to jaws 16, 18 along the first transverse edge of clamp 14, and alignment guide 46 is secured to the second transverse edge of clamp 14 and extends generally perpendicular to clamping faces 18, 22.

Figure 3A:
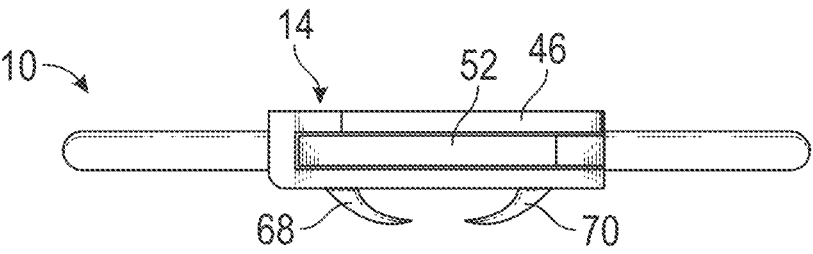
FIG. 3A is an end elevational view of the surgical clamp of FIG. 1, showing a first embodiment of wound compression prongs on an inferior surface of the arms.
Figure 3B:
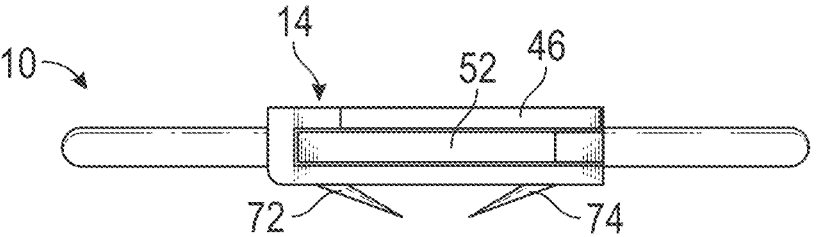
FIG. 3B is an end elevational view similar to FIG. 3A, but showing an alternative embodiment of the wound compression prongs.
Figure 4:
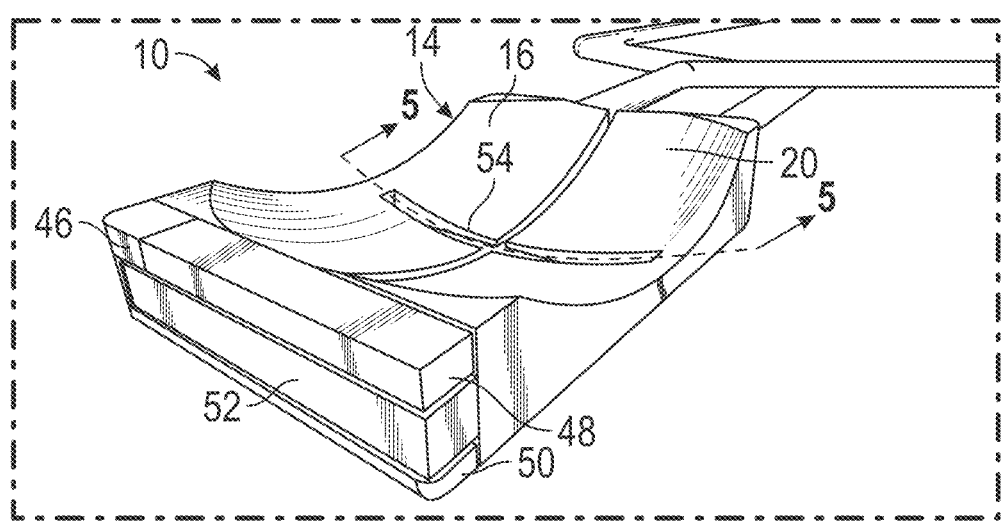
FIG. 4 is an enlarged perspective view of the clamp jaws and the distal end of the clip handle.

As shown in FIGS. 3A and 3B, some embodiments of clamp 14 also have compression members or prongs, such as clamping needles or barbs that extend from the inferior surface of the clamp. Multiple clamping needles or barbs can be arrayed in a row longitudinally along the inferior surface of each jaw 16, 20 with the barbs extending away from the inferior surface of the jaws toward target tissue to be clamped. The row of needles or barbs is preferably aligned parallel to and substantially equidistant from the clamping face of each jaw. The barbs or clamping needles have bases attached to the inferior surfaces of the jaws but taper to pointed or sharp tips for piercing tissue outside the margins of the wound or incision to assist in moving the underlying tissue together with the margins of the wound in apposition for clamping between clamping surfaces 18, 22. The barbs or needles at their bases generally extend at an included angle of 15-30 degrees to the inferior surface of the clamp toward the midline of the instrument or the margins of the wound to be closed. The barbs or needles extend parallel to one another, and all of them incline to the inferior surface of the clamp at substantially the same included angle. The barbs or needles on each jaw are substantially mirror images of each other, and their sharp tips point toward one another but do not completely meet when the jaws are closed.

An embodiment shown in FIG. 3A shows two opposing barbs that are curved from the base to the tip so that the barbs 68, 70 on the inferior surfaces of opposing jaws become nearly parallel to the inferior surface of clamp 14 as they approach the sharp tips. In the embodiment shown in FIG. 3B, straight compression needles 72, 74 extend from the inferior surface of each jaw with their sharp tips pointed in a direction that will pierce underlying tissue and help bring the margins of the incision or other wound into apposition as the jaws close.

Figure 9:
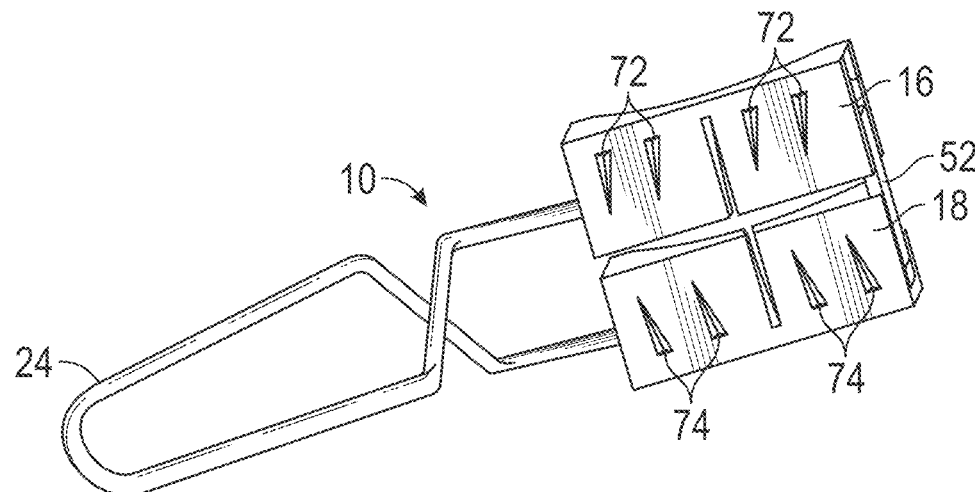
FIG. 9 is a bottom view of the embodiment shown in FIG. 3B, illustrating the orientation of closure needles on the inferior surface of the jaws.
Figure 10:
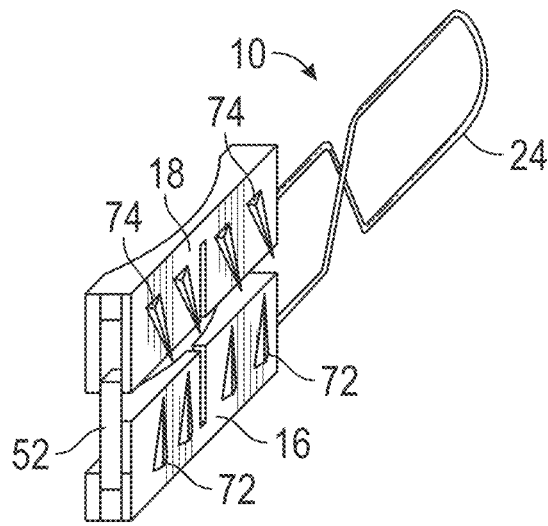
FIG. 10 is an end perspective view of the distal end of the clamp showing a first embodiment of a clamp alignment structure for maintaining the clamp in a substantially planar orientation with its arms aligned, and needle shaped compression prongs on the inferior surfaces of the clamp jaws.

The arrangement of rows of needles is illustrated in FIGS. 9 and 10, which show the inferior flat surface of jaws 16, 20 with a line of compression members arrayed along the inferior surface of each jaw. In the illustrated embodiment, the compression members are of the straight needle type that are fixed at their bases to the inferior surface of the jaws. The bases of needles 72 are secured to the inferior surface of jaw 16 and needles 72 extend substantially parallel to one another toward the plane along which clamping surfaces 18, 22 meet. A symmetric, mirror image set of needles 74 are secured to the inferior surface of jaw 18 and each of the needles within each set extends substantially parallel to one another toward the plane along which clamping surfaces 18, 22 meet. The tips of opposing needles generally point to a common point in space even though the opposing needles need not meet at that common point.

The needles or other prongs project sufficiently far from the inferior surface of the jaws to enable them to grab only underlying superficial tissue that is to be mobilized to align and appose the opposing margins of the incision or other wound, without penetrating the wall of the anatomic structure being clamped. For example, the needles are of a sufficient length and directed at a suitable angle to engage and move the conjunctiva and sclera of the opposing wound margins toward one another as the jaws close, without penetrating the wall of the eye and introducing perforations that would create transmural wounds that would themselves require repair to maintain the intraocular pressure in the eye.

In use, for example during a surgical procedure on the eye, an incision 78 (FIGS. 11A, 11B) is made through the wall of the eye 80 to gain access to the posterior chamber 82 of the eye, for example to perform a vitreoretinal procedure, such as surgery on the retina or transplantation of retinal transplant tissue. After the incision is made, the surgeon or other user grasps instrument 10 by handle 24 and positions the closed clamp 14 (FIG. 1) over the incision with clamping surfaces 18, 22 positioned over and aligned with the incision 78. Legs 32, 34 of handle 24 are then manually compressed toward one another to slide segments 40, 42 freely over one another and move legs 32, 34 closer to one another against the bias of handle 24. This action moves arms 28, 30 away from one another (FIG. 2) in a distance generally proportional to the degree of compression of handle 24. During this movement, alignment guide 46 maintains jaws 16, 20 in a relatively fixed position to one another, with clamp surfaces 18, 22 generally parallel to one another as the jaws slide away from each other in a common plane.

Figure 11A:
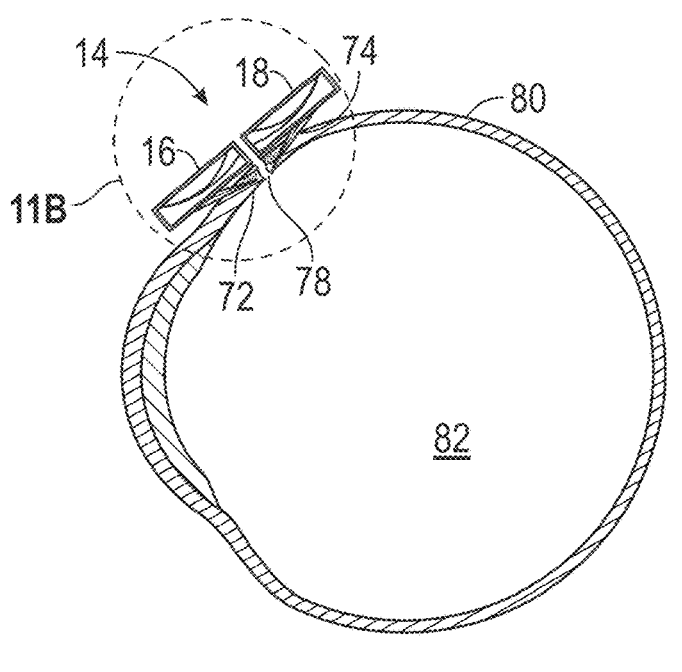
FIG. 11A is a schematic cross section of the eye showing the clamp closing a sclerotomy incision and the compression prongs compressing the tissue into apposition on either side of the surgical incision through the wall of the eye under the closed clamp.
Figure 11B:
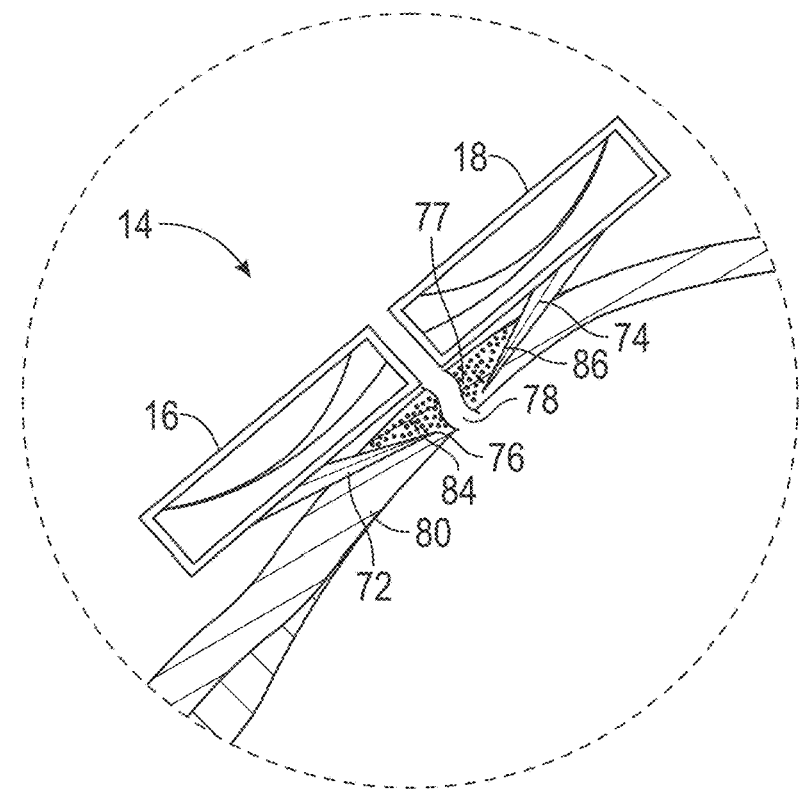
FIG. 11B is an enlarged view the surgical clamp shown in FIG. 11A, illustrating tissue margin alignment and hemostasis achieved by the compression needles of the closed clamp.

Once jaws 16, 20 are open, the inferior surfaces of jaws 16, 20 are placed firmly on the surface of the eye with barbs 68, 70 or needles 72, 74 engaging the tissue underneath the jaws. As illustrated in FIG. 11A, compression needles enter the wall of the eye adjacent opposite margins of the incision and the needles gradually enter more deeply into the wall of the eye 80 without perforating it as compression of handle 24 is released in a controlled manner, legs 32, 34 move apart because of their bias, and arms 28, 30 move toward one another to close jaws 16, 20 with clamp surfaces 18, 22 in apposition (FIGS. 1, 5 and 6). During these movements, compression needles 72, 74 mobilize the underlying tissue and pull the margins 76, 77 of the incision 78 toward one another to maintain a substantially fluid tight closure that avoids disrupting the pressure balance in the eye that could occur from loss through the sclerotomy of vitreous and other intraocular fluids. As illustrated in FIG. 11B, when the clamp is closed over the incision the tips of the needles 72, 74 are adjacent one another. The needles help achieve hemostasis by compressing the scleral tissue between the needles and the inferior surface of the clamps that rests on the eye, and compressing tissue between opposing needles to diminish perfusion of the tissue. An area of diminished perfusion (and improved hemostasis) is shown by shaded areas 84, 86 in FIG. 11B.

In some vitreoretinal and other procedures it is desirable to repeatedly open and close the incision to introduce and withdraw instruments through the incision. To open the clamp from the closed position shown in FIG. 1, handle 24 is compressed as described previously to move legs 32, 34 toward one another and arms 28, 30 and jaws 16, 20 apart. The clamp may then again be closed by releasing the compressive force on the handle.

The illustrated embodiment of the clamp shown in FIGS. 1-6 is made of surgical metal, such as surgical stainless steel, is 4-5 mm wide, 4-5 mm long, and 1-2 mm thick. For example, a specific embodiment would be approximately 4.5 mm wide, 4 mm long, and 1 mm thick. Modifications can be made to the dimensions of the clamp design in clamp size, curvature of the clamp body, orientation and design of the spring clip handle, as well as placement and numbers of suture guides. The clamp can be adapted for a variety of surgical procedures, for example for other types of wounds or incisions in blood vessels, intestines and skin wounds. The jaws of the clamp can be configured to approximately or substantially conform to an anatomic structure to be clamped. For example, the inferior surfaces of the jaws that clamp the anatomic structure are curved to substantially conform to a curved anatomic structure such as the wall of a blood vessel or intestine, or the inferior surfaces of the jaw may be flat to fit against a more planar surface such as an expanse of skin that approximates a plane. Also, the spring clip handle can be squeezed to two or more clamp positions, such as the unset and set position. The clamp can also be a sterilized clamp for use in a surgical procedure, and it can be cleaned, re-sterilized and re-used if desired.

Figure 7:
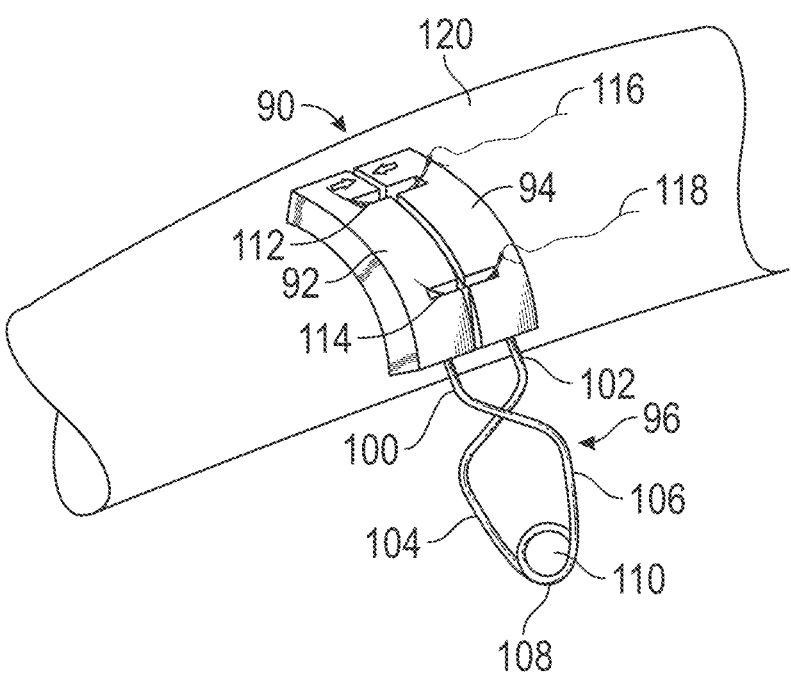
FIG. 7 is a perspective view of another embodiment of the surgical clamp applied to the wall of a curved structure, such as a hollow viscus or blood vessel to temporarily close an incision or wound.

To illustrate some of these variations, an alternative embodiment of the clamp is shown in FIG. 7 in which clamp 90 has two elongated curved jaws 92, 94 that meet at a clamping junction that bisects clamp 90 longitudinally, and a handle 96 for opening and closing this embodiment of the clamp. The handle includes first arm 100 secured to jaw 92 and a second, substantially parallel arm 102 secured to jaw 94, as well as a leg 104 for arm 102 and a leg 106 for arm 100. Legs 104, 106 meet at apex 108. This embodiment of spring clip handle 96 differs from the earlier depicted embodiment by having a tension coil 110 incorporated into handle 96 to increase the spring bias force that closes jaws 92, 94 of clamp 14. For example, handle 96 is a single continuous wire member that is bent into the crossed configuration shown in FIG. 7, with an additional circular bend at apex 110 to improve the bias of handle 96.

This embodiment of the clamp includes a plurality of suture guide slots. In FIG. 7, a pair of suture guide slots 112, 114 extend through the clamp transversely across the clamp and the clamping junction between elongated jaws 92, 94. Guide slots 112, 114 each have a portion of the slot in each of elongated jaws 92, 94 such that the guide slots are cooperatively formed by the slot portions in each jaw. In this instance the length of each slot is divided equally between each jaw. FIG. 7 illustrates a suture 116 being placed in guide slot 112 and another suture 118 being placed in guide slot 114 by a curved needle that enters each guide slot at one end of the slot in jaw 94 and exits the same guide slot at its opposite end in jaw 92.

Clamp 90 in FIG. 7 is illustrated in use on the wall of a curved structure 120, such as the wall of an intestine or blood vessel. Jaws 92, 94 are of substantially the same thickness, and each have an inferior curved surface that is placed on curved structure 112 and an opposite, superior curved surface through which sutures 116, 118 are introduced to close an incision or other wound beneath the clamping junction. The superior and inferior surfaces of the jaws are both curved and have a similar radius of curvature about a common center point. The particular curvature of the surfaces of jaws 92, 94 is selected to conform to a curved anatomic structure to which clamp 90 is to be applied for clamping a wound. Clamp 90 is then closed over the incision in the manner previously described using the bias of spring-loaded handle 96, by releasing compression force on legs 104, 106 of handle 96.

Figure 8:
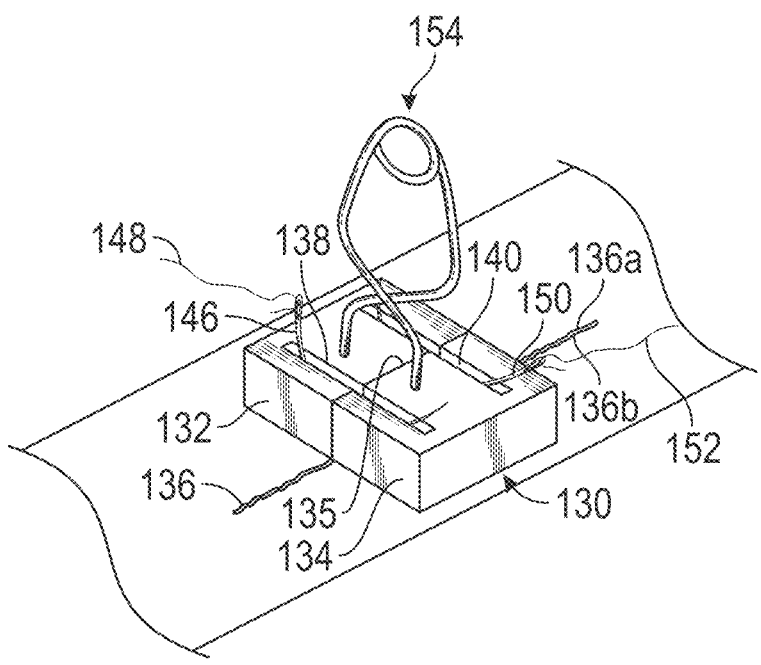
FIG. 8 is a perspective view of another embodiment of the surgical clamp applied to a substantially planar surface area such as the skin.

FIG. 8 illustrates yet another embodiment, in which clamp 130 includes a pair of elongated, cuboidal or rectangular block-shaped jaws 132, 134 that meet along a clamping junction 135 placed over an incision 136 having margins 136*a*, 136*b* brought into apposition by clamp 130. A pair of suture guide slots 138, 140 extend transversely across jaws 132, 134 through clamping junction 135. A curved suture needle 142 is shown entering a first end and exiting a second end of guide slot 138 carrying a suture 144 for placement across the margins 136*a*, 136*b*. A second curved suture needle 150 carrying an attached suture 152 is shown entering the second end and exiting the first end of guide slot 140. Handle 154 is operable as previously described to open jaws 132, 134 against the bias of handle 154 by compressing the legs of the handle, and then close jaws 132, 134 by removing the compression.

FIGS. 12A-12D illustrate yet another embodiment of the surgical instrument. Clamp 230 includes a pair of narrow elongated curved or arcuate jaws 218, 220 that are aligned to form mirror image flat parallel faces that meet along clamping junction 235. Each of the jaws has the same radius of curvature, for example about 12 mm, and the jaws are each narrow in width (for example 1.5 mm). The curves of the jaws causes their free ends to be higher than the handles, elevating the tips of the jaws above the plane of the handled formed by the wire frame. For example, the tips of the jaw are elevated about 30 degrees with respect to the plane of the wire frame handle.

Each jaw face of jaws 218, 220 contains mirror image recesses that cooperatively form a central circular aperture or opening 237 (forming a port to access the eye cavity without opening the clamp) for placement of some surgical instruments through. The handle of the instrument includes arms 228, 230 and legs 232, 234 that meet at apex 254 that resiliently biases legs 232, 234 into a non-parallel relationship away from one another and biases arms 228, 230 and jaws 218, 220 toward one another into a parallel relationship. An intermediate portion of the instrument, between the legs and arms, forms an alignment guide that maintains the opposing mirror image faces of the jaws in a substantially aligned orientation to one another, for example substantially parallel to one another, and resists torqueing forces that would twist the first and second clamping surface out of alignment. The alignment guide is formed by bending the wire frame of the instrument, such as legs 232, 234 and/or arms 228, 230. In the illustrated example, the alignment guide is formed by a bent portion of the wires that form the intermediate portion 238 of the surgical instrument. The wire frame of each of legs 232, 234 is bent into loops 256, 258 that form opposing finger grips 256, 258 against which the fingertips of an operator may press to open the clamp.

Figure 12A:
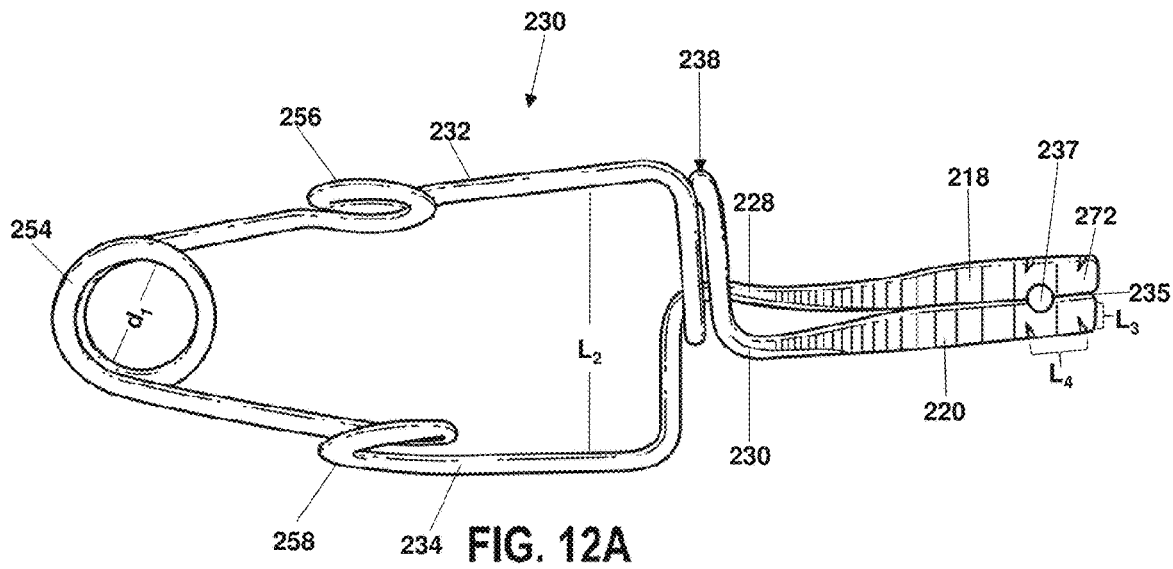
FIGS. 12A through 12D illustrate another embodiment of the surgical clamp in which the jaws are curved to achieve a tighter seal of the wound, and an intermediate portion of the wire clip is bent to form a guide channel to maintain the jaws in a desired alignment as the clamp is opened and closed. The narrow width of the clamp jaws also minimizes obstruction of the surgical field and microscope view. Placing the guide channel in the handle (instead of the jaws) minimizes inadvertent trauma to underlying tissue while allowing the arms of the handle to move apart in the plane of the channel to maintain a predetermined alignment of the jaws as they move away and toward one another. For example, opposing faces of the jaws are maintained substantially parallel to one another as the jaws move. A small aperture through the jaws permits smaller bore instruments to be placed directly through the jaws; larger instruments are introduced into the eye by opening the jaws of the clamp.
Figure 12B:
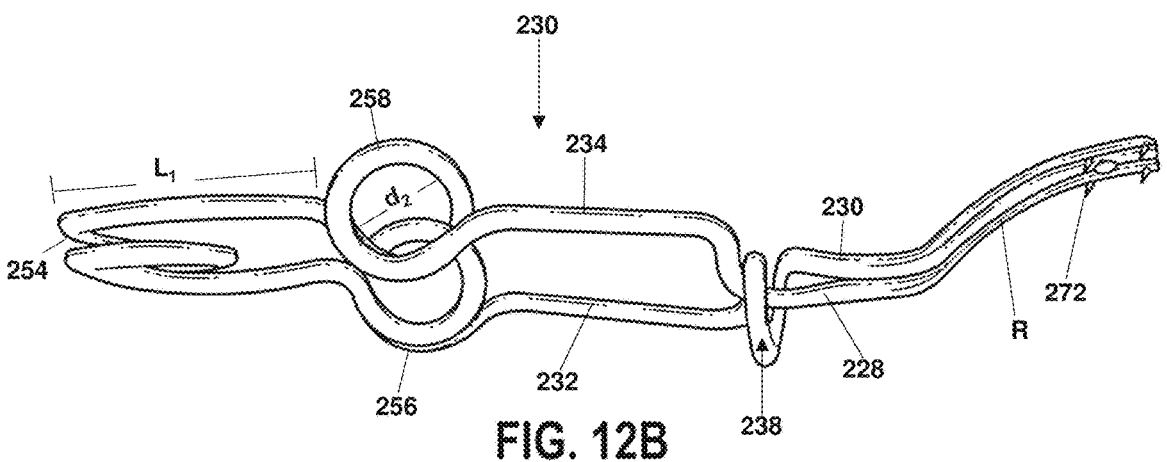
Figure 12C:
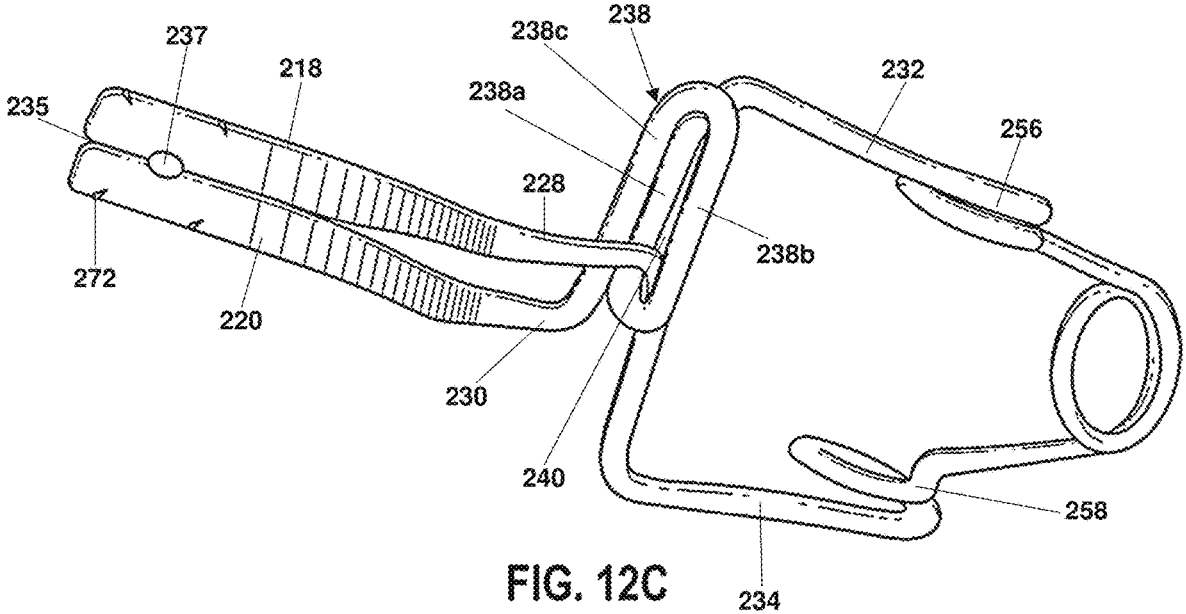
Figure 12D:
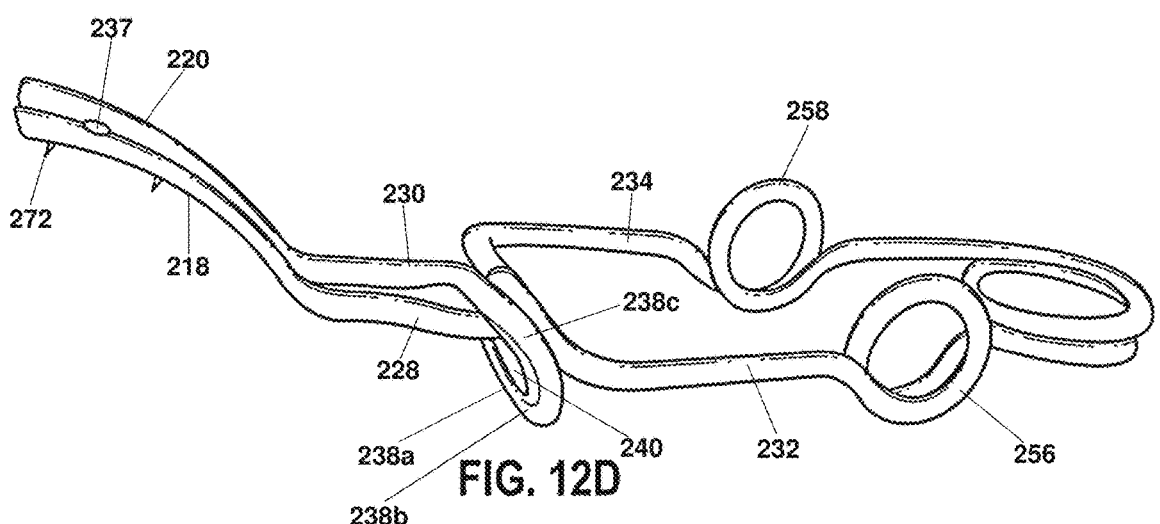

As shown in FIG. 12C, intermediate portion 238 may be formed from the wire of leg 234 by bending the wire through an arc at an angle of about 90 degrees from leg 234 toward the midline of the instrument and slightly past arm 228 to form first straight segment 238a, then through an arc around arm 228 and back upon itself at an angle of about 180 degrees to form second straight segment 238b that is slightly spaced from and substantially parallel to segment 238a to form a guide channel 240 therebetween. The wire is then bent again through an arc back upon itself again to form a third straight segment 238c that is adjacent and parallel to first segment 238a. Third segment 238c extends toward the midline of the instrument and past arm 228 at which point it bends through an arc at an angle of about 90 degrees to orient arm 230 substantially parallel to arm 228 with opposing mirror image faces of the jaws in abutment. With arms 228, 230 parallel to one another jaws 218, 220 are held in a fixed predetermined orientation to one another with their opposing faces substantially parallel along clamping junction 235 when jaws 218, 220 are closed.

In use, clamp 230 is opened by compressing legs 232, 234 toward one another against the bias of apex 254 with arm 228 sliding in channel 240 away from arm 230 while maintaining a predetermined desired alignment (for example the substantially parallel relationship) of the opposing mirror image faces of jaws 232, 234. After placement of the instrument in a clamping position with respect to an incision, the compression of legs 232, 234 is discontinued to allow the legs to move to their normally biased positions away from one another as arm 228 slides in guide channel 240 toward arm 230. Jaws 232, 234 have barbs 272 on their curved inferior surface that engage the underlying tissue and assist in movement of the edges of the incision toward one another to be clamped by jaws.

In use, the clamp is applied to a wound, such as a surgical incision, to close the wound. In a particular example the wound is a surgical incision in the eye, for example in the sclera, and the curvature of the jaws is selected to conform that curvature of the jaws to the curvature of the underlying eye. The barbed clamp surface is placed on the edges of the incision to pull the edges toward one another as the jaws are moved toward one another in response to the bias of spring 254. Once the jaws are closed, the incision is sealed except for circular opening 237 that provides an access port through which some instruments (such as a vitreous cutter or retinal scissors or some other standard instruments used in surgery) may be introduced into the eye while retaining sufficient intraocular pressure within the eye during the surgical procedure.

Without being limited to any particular dimensions, the following dimensions illustrate one particular example of the instrument shown in FIGS. 12A-12B that is used for selectively sealing incisions of the eye. As shown in FIG. 12A, spring 254 has an inner radius $d_1$ of about 4-6 mm, for example 5 mm, while the inner radius of the finger grips have an inner diameter $d_2$ of about 3-5 mm, for example 4 mm. The jaws are curved at a radius of curvature R of about 10-14 mm, for example 12 mm, the width $L_3$ of each jaw is about 1-3 mm, for example 1.5 mm, and the distance $L_4$ between barbs 272 is about 1-3 mm, for example 2 mm. The diameter of the opening 237 is about 0.6-1 mm, for example 0.8 mm. As shown in FIG. 12B, the curve of the jaws raises them through an arc out of the plane of the guide channel formed by intermediate portion 238.

Figure 14A:
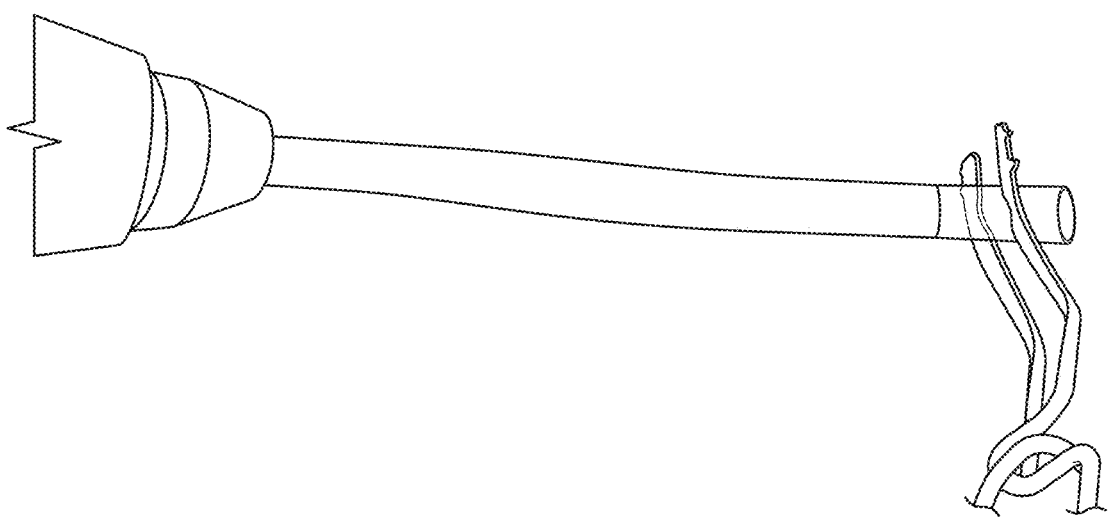
FIGS. 14A through 14D are digital images that illustrate use of the instrument of FIG. 12.
Figure 14B:
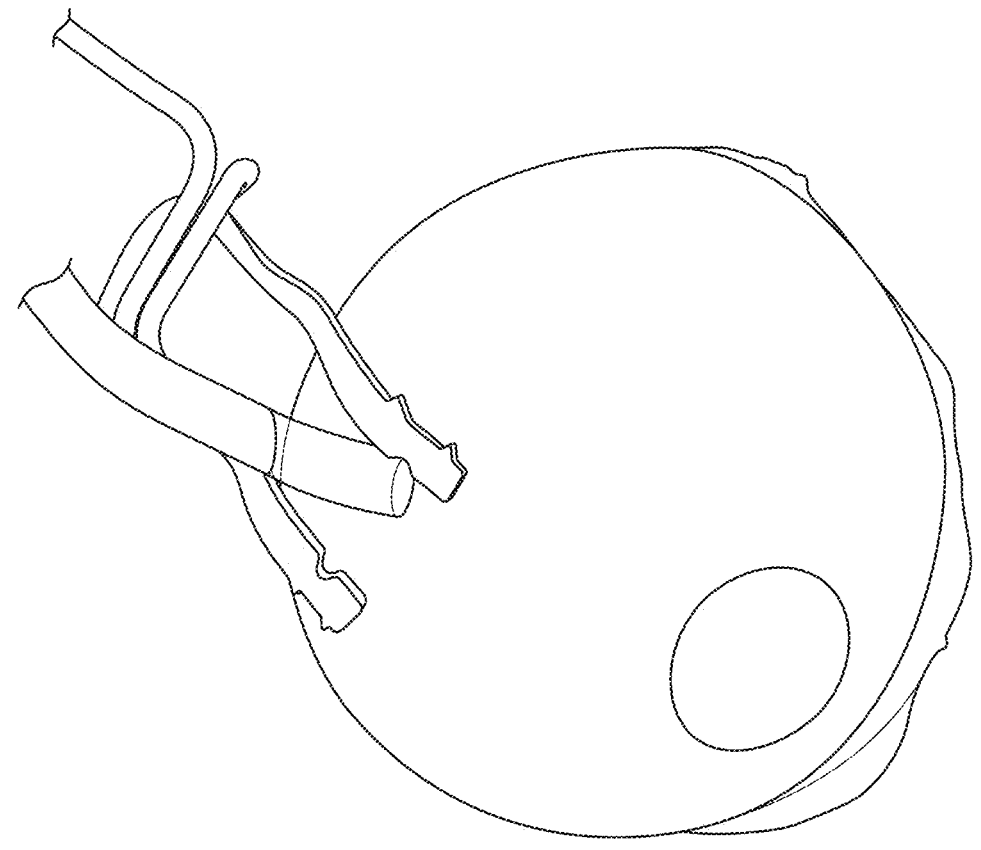
Figure 14C:
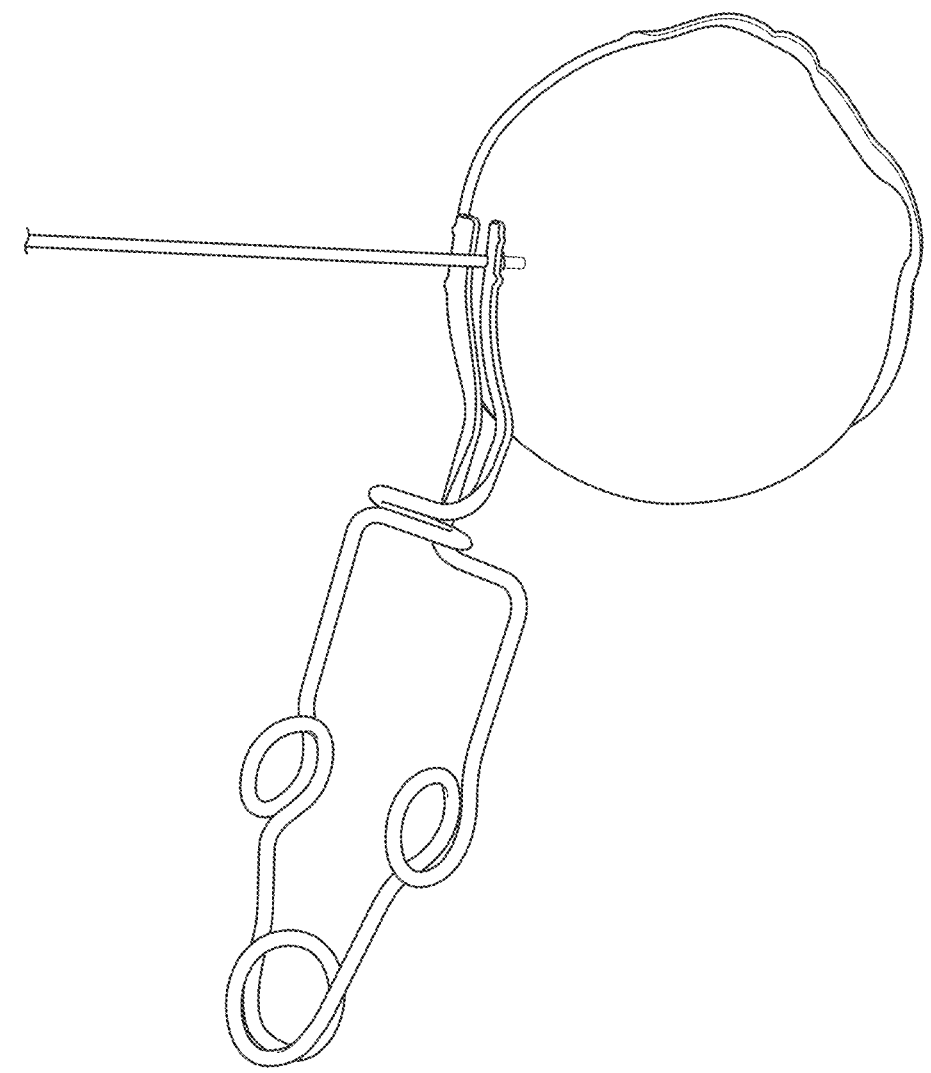
Figure 14D:
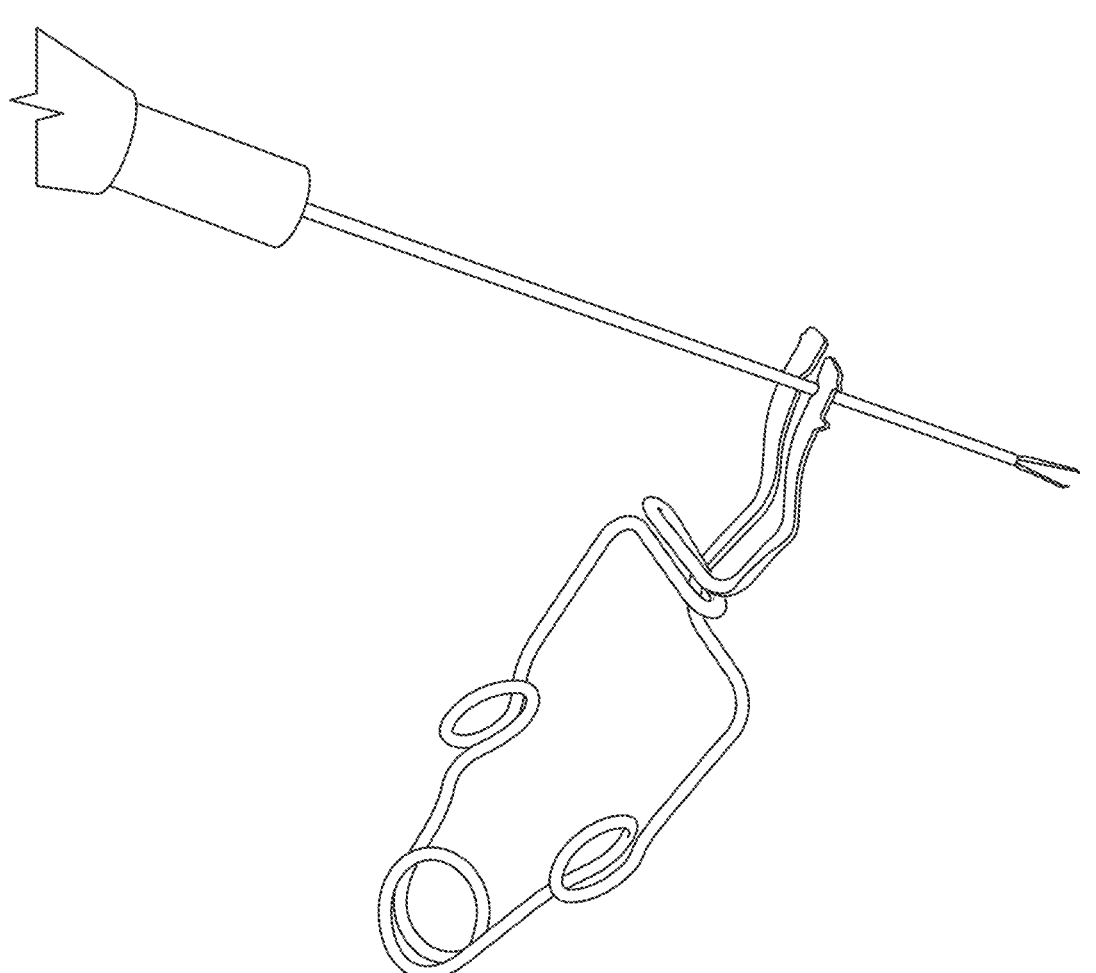

FIG. 14A illustrates the clamp 230 with jaws 218, 220 opened for insertion of a tubular transplant instrument between the opened jaws. FIG. 14B illustrates how the clamp 230 would be positioned on the surface of a substantially spherical eye with the curved arms of the jaws substantially conforming to the curvature of the eye surface to steady the instrument while pressure is applied to its legs to maintain the clamp in the illustrated open position. FIG. 14C illustrates use of clamp 230 with a smaller diameter instrument, such as a vitreous cutter (vitrector). Since the diameter of the illustrated instrument is smaller than the diameter of the opening 237, the vitreous cutter is inserted through opening 237 without opening the jaws. FIG. 14D illustrates how the clamp 230 would be positioned on the surface of the eye to close an underlying incision in the eye while the instrument is placed through the jaws with the curved under surface of the jaws conforming to and resting upon the curved surface of the eye.

The illustrated surgical clamps may be used in many different types of surgeries and medical procedures. In the eye, for example, the clamp may be used to deliver cell-based therapies or retina-stimulating implants for treating eye conditions such as age-related macular degeneration (AMD), geographic atrophy (GA), retinitis pigmentosa (RP) by delivering sheets of retinal pigment epithelium (RPE), retina and/or choroid such as newly grown RPE, or an engineered blood-retina barrier implant. These surgeries are performed through large sclerotomies in the eye to deliver sufficient tissue into the eye, however the large sclerotomy poses an increased risk of eye collapse, retinal detachments, and bleeding due to loss of intraocular pressure (IOP). Although IOP can be maintained by an infusion of fluid into the eye, it is advantageous not to infuse excessive amounts of fluid during the surgery. Unfortunately, the large incision must often be left open for extended periods of time to introduce, remove and reintroduce instruments into the eye at spaced intervals during the surgical procedure. The clamp disclosed herein minimizes the risks attendant this procedure by providing a tool that can quickly close large eye wounds to maintain and stabilize IOP, help stop bleeding, maintain precise tissue alignment of wound margins, and provide a guide for suture placement having controlled depth and distance from the tissue margins.

An example of a particular procedure in which the clamp can be used is illustrated in the following example.

Example 1

Surgical Procedure For Scaffold Implantation

This example illustrates a procedure for implanting or transplanting retinal tissue or scaffolding into the eye. This specific example illustrates implantation of a retinal pigment epithelium sheet on a biodegradable scaffold into the subretinal space (FIGS. 13A through 13H). This particular example is of the procedure in a pig eye, but the same or similar procedure could be used to perform the surgery in subjects of different species (such as humans). The example includes a method for creating a retinotomy at the base of a retinal detachment, which is then treated by implantation of a choroid/retinal pigment epithelium scaffold on which three-dimensional retinal tissue can develop.

Five to seven days prior to surgery, blood vessels are cauterized with a surgical laser using an indirect ophthalmoscope in the area of the choroid at the site of an intended large sclerotomy. Cauterization of the blood vessels reduces bleeding at the site of the subsequent large scleral incision.

On the day of surgery, the pig's eye is cleaned using povidone iodine 5% while surrounding skin is cleaned using povidone iodine 10%. A temporal canthotomy is performed with scissors and the nictitating membrane is retracted using 4-0 braided silk to increase the exposure area if needed. Surgical ports are created at 3.5 mm from the limbus using 25G valved cannulas. A posterior vitreous detachment is performed in a laser-injured area (see Example 3) and vitrectomy is performed. The blood pressure is taken to determine whether it is in a desired range; if needed, pressure lowering drugs are administered to lower systolic blood pressure <100 mmHg.

Figures 13A, 13B:
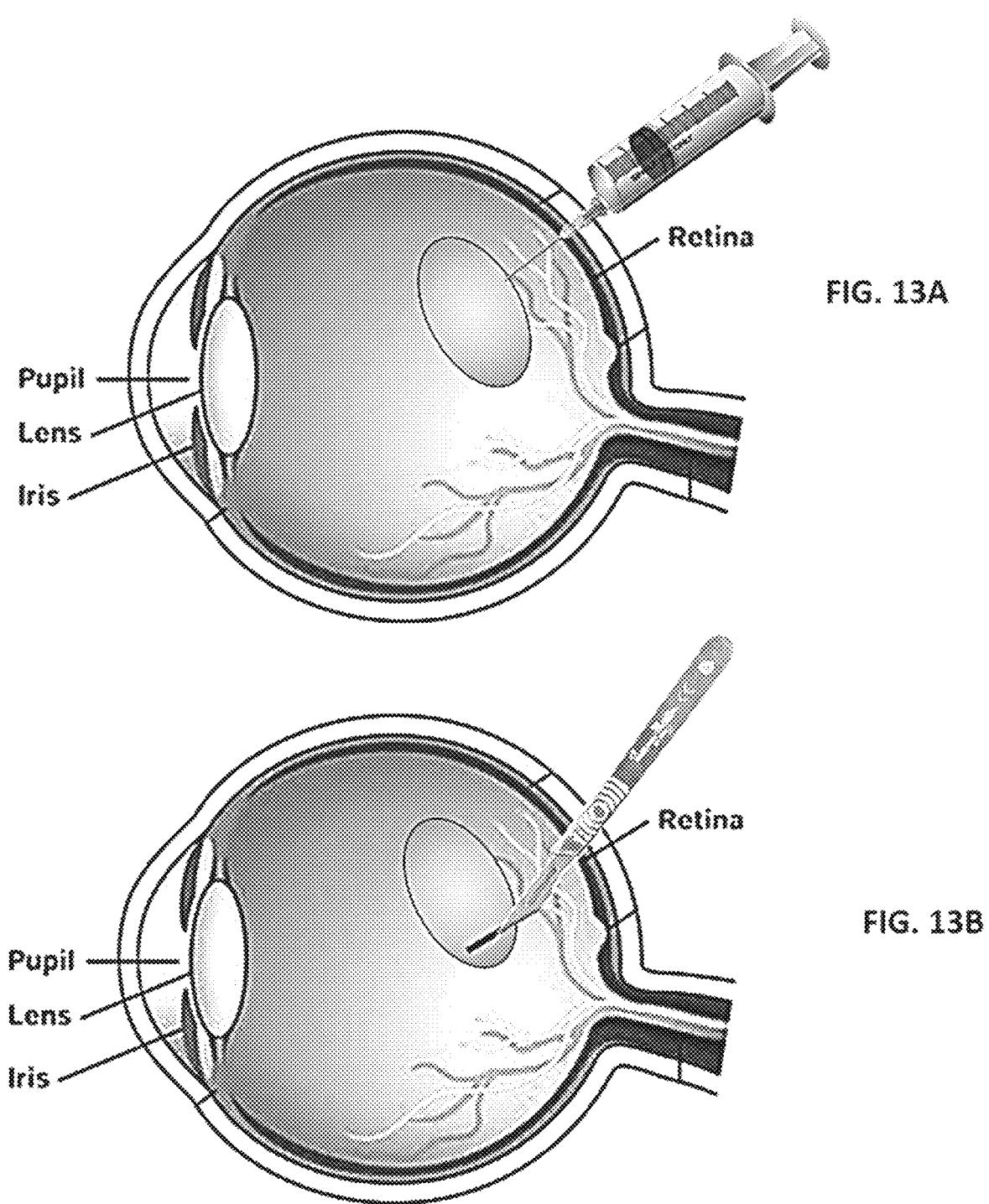

As shown in FIG. 13A, a localized retinal detachment is induced with a 38G polyamide cannula and injecting Hank's Balanced Salt Solution (HBSS). A scissor retinotomy is performed in the base of the retinal detachment, and the detachment is reinforced with 0.21% Healon GV using a blunt tip cannula. A second small posterior retinotomy is performed using a 25G endocautery tip accompanied by momentary action of a vitrector (FIG. 13B) to create an implant entry port.

The sclera is exposed by a conjunctival (nasal-side) periotomy around a port to accommodate an enlarged implantation tool, such as the implantation tool described in WO2016/007852. An incision is made in the sclera (FIG. 13C) to allow the transplantation tool to be inserted into the eye cavity. The clamp is applied to the scleral incision site to maintain intraocular pressure. Since a relatively large scleral incision is made for introducing the implantation instrument described above, the disclosed clamp helps maintain a pressurized eye when the implantation tool is not in the eye. The clamp is partially opened and a sclerotomy of 2.5 mm is performed at the site of the surgical port to accommodate the transplantation tool cannula. The handle of the tool can be manipulated (for example compressed) to partially open the jaw to perform the sclerotomy. Tissue grabbing prongs on the bottom faces of the jaw can help maintain the opposing edges of the sclerotomy wound in relatively close apposition while the incision is made. Compressive force on the handle may then be released to completely close the wound if needed, for example while loading material for transplantation in the tool.

Figures 13C, 13D:
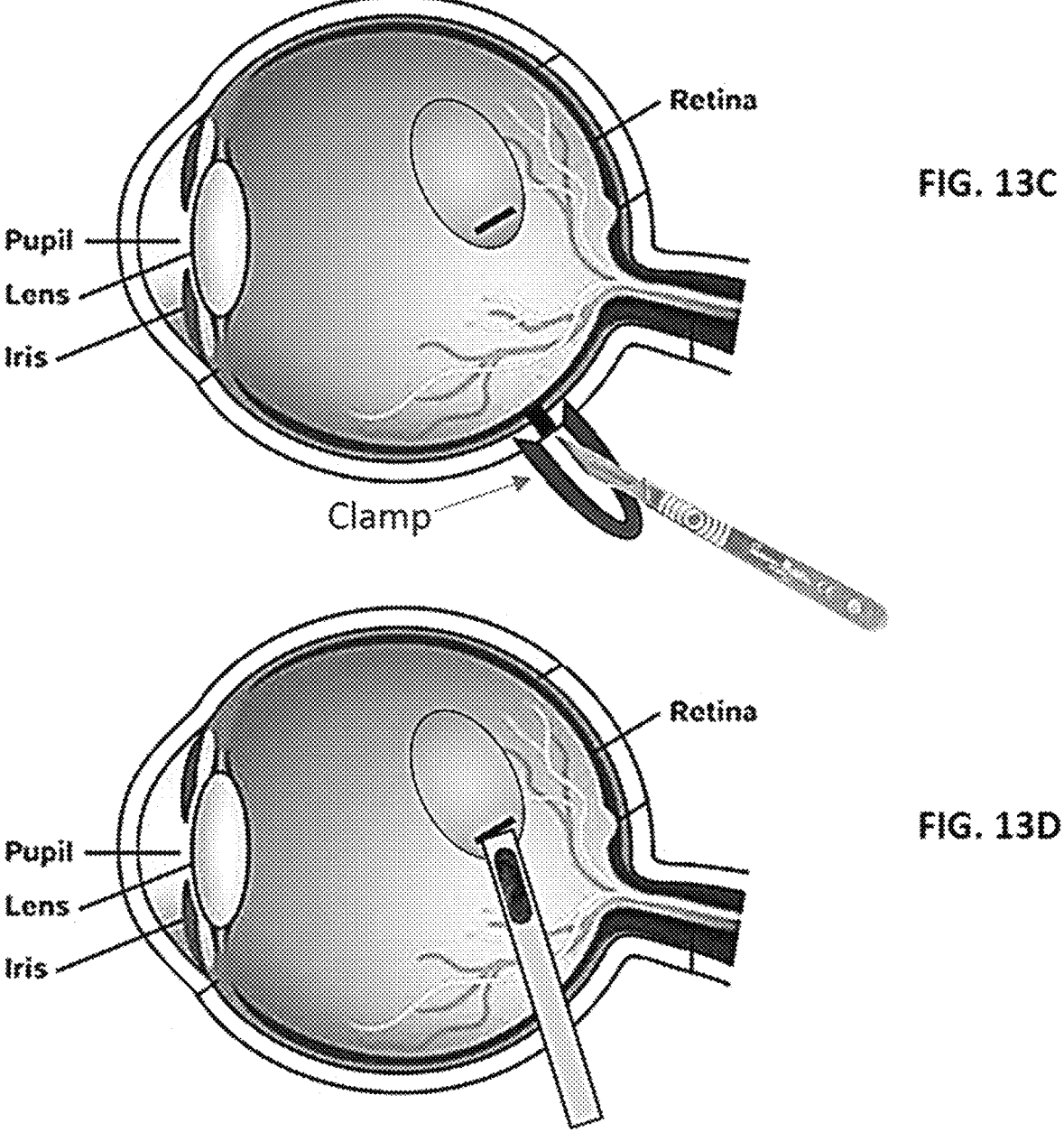
Figures 13E, 13F:
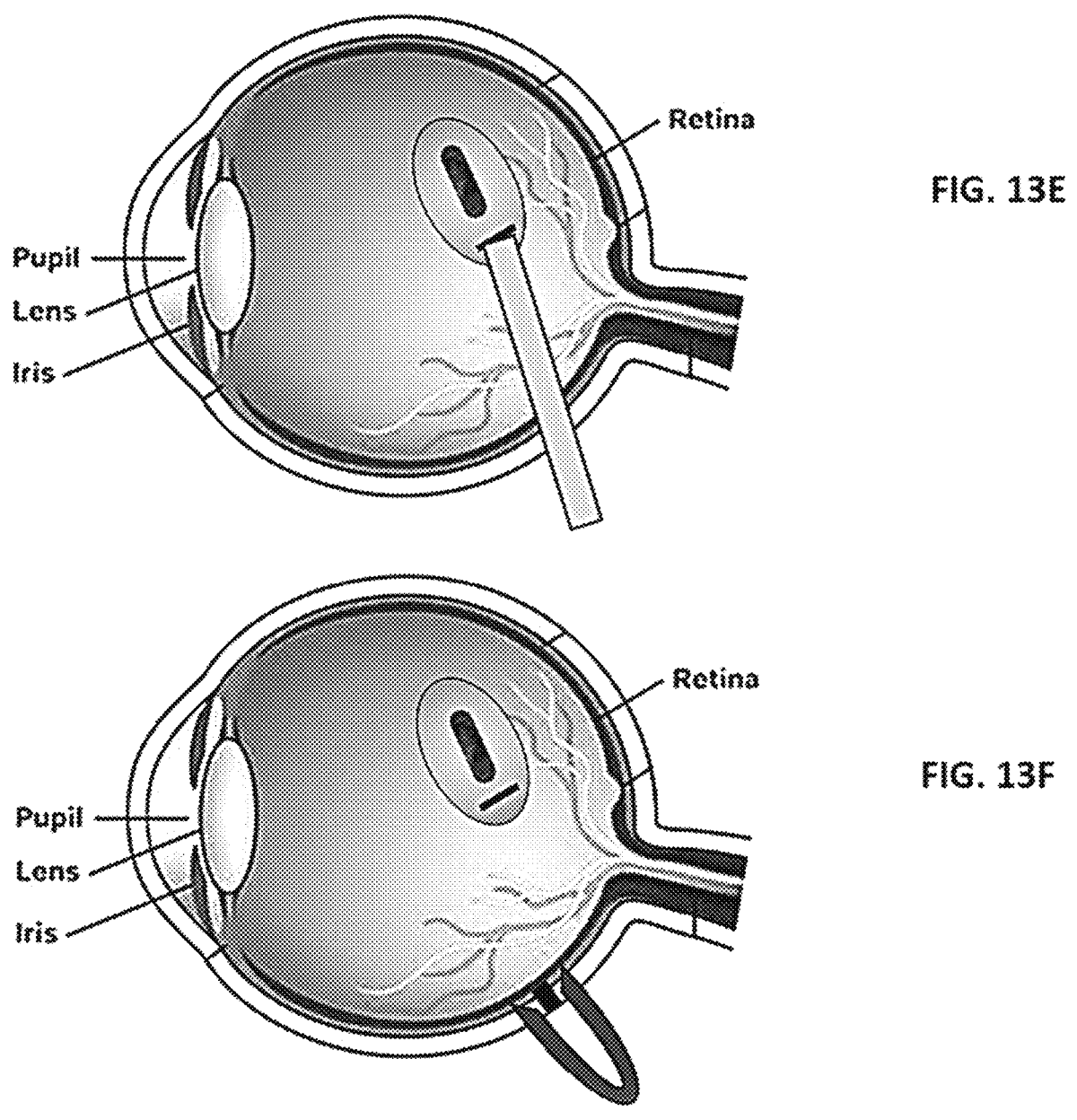
Figures 13G, 13H:
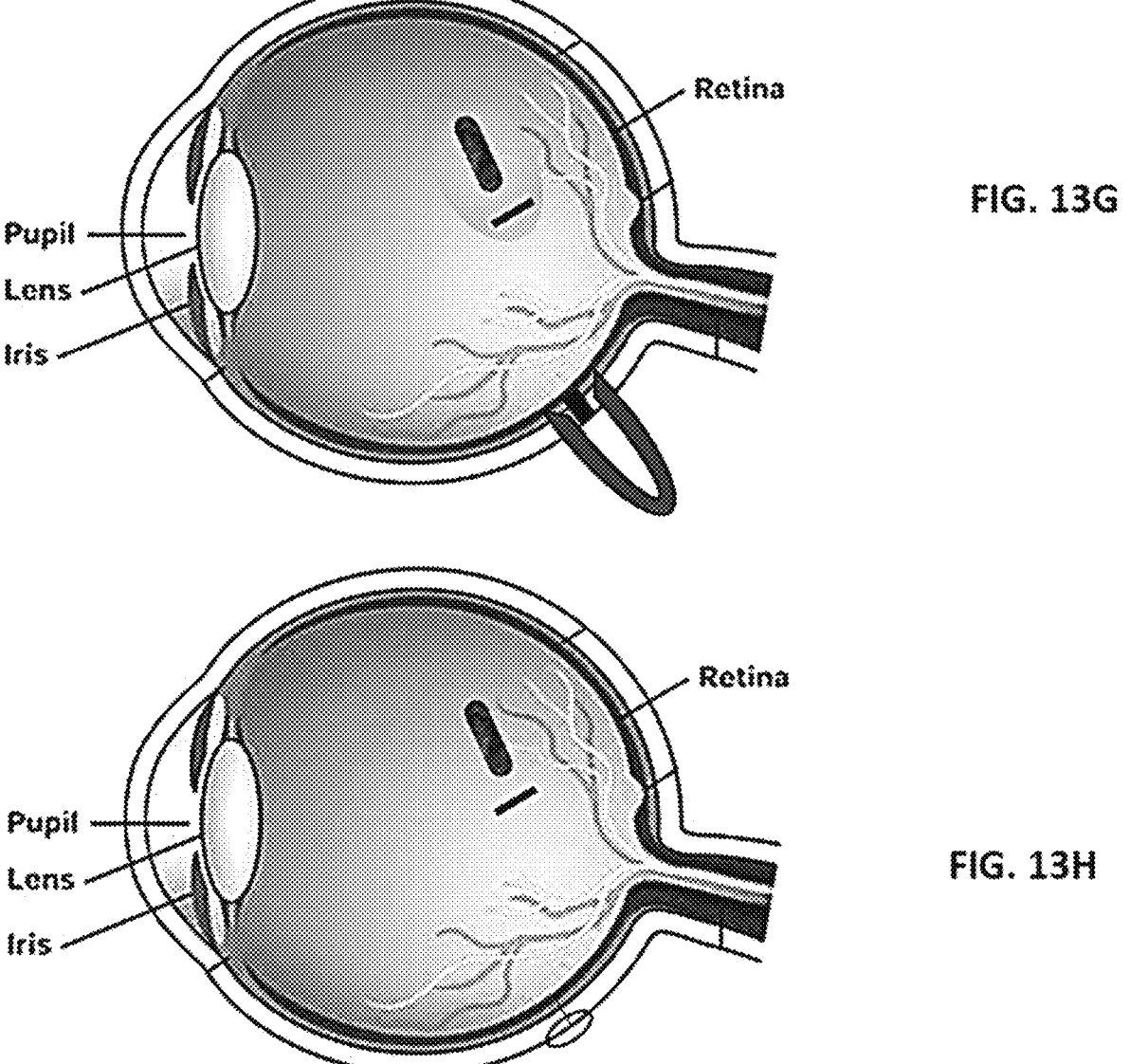

The tool is loaded with the material for transplantation (such as a scaffold or tissue or implant), and the clamp is completely opened to introduce the tip of the transplantation tool through the sclerotomy. The tool comprises a handle and a flat shaped tip. Sheets of tissue or implants can be vacuumed into a delivery aperture of the tip where the tissue is selectively retained by a suction force (FIG. 13D). The clamp is then removed from the scleral incision, the injector portion is advanced into the eye, and the tool tip is aligned with the incision in the retina. The implant tip is then placed under the retina (FIG. 13E) and the implant is expelled from the tool into the subretinal space that has been formed. The tool delivers the retained tissue to a site of implantation by discontinuing the vacuum and instead applying an injection force through the aperture. The scaffold or tissue or implant is completely ejected (FIG. 13E) using a VFI function and pedal switch. After implantation is complete, the implantation tool is retracted, and the clamp is reapplied to the scleral incision quickly thereafter (FIG. 13F).

Heavy liquid solution (e.g. PERFLUORON®) or fluid air exchange is used to flatten the retina over the transplanted area (FIG. 13G), and the retinotomy is closed by gentle apposition of retinotomy borders without retinopexia. A first/central large sclerotomy suture is applied through the suture guide slot of the clamp with Nylon 8-0. The clamp is removed and the sclerotomy site is completely sutured with Nylon 8-0. All valved cannulas are removed from the eye, the nasal conjunctiva is sutured with Vicryl 7-0, and the canthotomy is closed with Vicryl 5-0 FIG. 13H).

Immediately postoperatively, subconjunctival 0.1 mL Depomedrol (20 mg/mL0 and 0.4 mL Gentamicin (100 mg/mL) are administered. Ketoprofen 3 m/kg IM is administered for 3 days twice a day post-transplantation, and Triple Antibiotic Ophthalmic ointment is applied locally on the surgery eye for 5 days twice a day. An eye patch is applied to the post-operative eye for 12 hours to guard it. Valium (5 mg/ml) is administered 1 mg/kg in a slow intravenous drip.

When the animal is breathing without assistance, the animal is taken to the holding cage and placed in it in a lateral recumbent position with the surgical eye up. Immediately before extubating, Acepromazine (10 ml) is given in a dose of 1 mg/kg intramuscularly. By the evening meal at 6 pm (or earlier, if sedation does not seem to be sufficient) the animal receives Acepromazine oral 1.5 mg/kg, Diphenhydramine oral 4 mg/kg and Lorazepam oral 0.15 mg/kg. These three oral drugs are administered twice a day at the same doses two more full days.

Example 2

Post-Operative Immunosuppression

To minimize post-operative rejection of the implant and inflammation, an immunosuppression protocol may be used. The immunosuppression protocol is initiated at least one week prior to surgery to effectively suppress the immune system before a xenograft or allograft is introduced into the eye. The protocol can use a mixture of antibiotics that suppress microglial infiltration, as well as immumodulator drugs such as corticosteroids and other immunosuppressants (such as MTOR inhibitors). Such a protocol may be the following, in which BID means twice a day, SID means once a day, and IM means intramuscular. Any subset or combination of these drugs may be administered, but in this particular non-limiting example all the following drugs are administered as part of the immunosuppression protocol.

Doxycycline (100 mg/tab) 2 tabs BID (400 mg/day) until the day of euthanasia [antibiotic that also suppresses microglia infiltration].

Minocycline (100 mg/tab) 2 tabs BID (400 mg/day) until the day of euthanasia [antibiotic that also suppresses microglia infiltration].

Depo-Medrol (Methylprednisolone) (40 mg/ml) 5 mg/kg IM one time injection given on the first day [steroid for innate immune suppression].

Prednisone (50 mg/tab) 5 mg/kg SID started 2nd day of the immunosuppression regimen. This dose is continued for 4 weeks post-surgery after which it is tapered over 2 weeks period [steroid for innate immune suppression].

Rapamycin (Sirolimus) (1 mg/tab) 2 tabs SID on day 1 of the immunosuppression regimen followed by (0.5 mg/tab) 2 tabs SID until the day of euthanasia [long term immunosuppressor for adaptive immunity].

Tacrolimus (0.5 mg/tab) 1 tab SID until the day of euthanasia [slow release immunosuppressor for adaptive immunity].

Example 3

Laser Injury

As noted in Example 1, five to seven days prior to surgery, blood vessels are cauterized with a surgical laser using an indirect ophthalmoscope in the area of the choroid at the site of a planned large sclerotomy incision. Alternatively, diathermy may be used. Cauterization of the blood vessels reduces bleeding at the site of the subsequent large scleral incision.

A separate laser procedure is used to selectively damage RPE or RPE and retina or RPE, retina, and choroidal blood vessels at the site of implantation of the implant, such implantation of an engineered blood retina barrier implant or a retina or an artificial retina. This procedure requires titration of the dose of laser injury to achieve its desired effect. For example, an IQ 532TM nm micropulsed laser (Index, USA) with a TxCell™ Scanning laser delivery system is used to selectively damage the retinal pigment epithelium (RPE). A "Threshold Test" is performed on each eye. Micropulsed power sufficient to obtain a barely visible whitening of the lasered retina in a 3×3 confluent test grid is identified. This threshold value is dependent on the pigmentation of the eye and is therefore used to cause the laser injury in this example. Exposure times of 330 milliseconds and 1% duty cycles are used to allow delivery of 33 micropulses per series, 10 ms each micropulse (0.100 on 9.900 ms off). For purposes of illustrating the method, the laser injury is induced at the visual streak (high density of cones) close to the optic nerve head. Laser spots that are 200 μm in diameter are formed using twenty-five 7×7 confluent grids to create a 38.5 mm² confluent lesion. A Volk HR centralis contact lens attached to a metal handle is used to avoid hand movements during the procedure.

At the end of the procedure, a non-steroidal anti-inflammatory drug (NSAID) such as Ketoprofen (100 mg/mL) 3 mg/kg IM is administered. Triple antibiotic ophthalmic ointment is applied locally post-laser injury for 3 days SID.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A surgical instrument for clamping a target structure, comprising:

a clamp having a first jaw forming a first clamping surface, and a second jaw forming a second clamping surface that opposes the first clamping surface; and a handle connecting the first and second jaws wherein the handle comprises an arm portion and a leg portion, wherein the arm portion comprises first and second substantially parallel arms that are respectively connected to the first jaw and the second jaw, and the leg portion comprises first and second legs that join at a common apex of the leg portion with a resilient bias that resiliently biases the first clamping surface and second clamping surface against each other into a substantially closed relationship for clamping the target structure, the first and second legs being disposed in a plane that extends at an angle to the first and second jaws of the clamp;

wherein the handle is compressibly movable to overcome the resilient bias and open the clamp by moving the first jaw and/or the second jaw to an open position while maintaining the first clamping surface and the second clamping surface in a substantially aligned orientation relative to one another, compression of the first and second legs of the handle toward each other moving the first and second arms against the resilient bias to open the jaws;

wherein the clamp has an inferior surface forming respective inferior surfaces of each jaw for resting on tissue to be clamped, and an opposing superior surface for facing upwardly away from the tissue to be clamped, wherein the clamp further comprises compression prongs that extend downwardly from the inferior surface of each jaw for extending toward an incision to be closed.

2. The surgical instrument of claim 1, wherein the handle comprises an intermediate portion between the arm portion and the leg portion, wherein the intermediate portion crosses over itself whereby compression of the leg portion to move the first and second legs toward one another overcomes the resilient bias to move the first and second arms away from one another, thereby moving the first and second jaws of the clamp away from one another.

3. The surgical instrument of claim 1, wherein the handle is a single continuous length of resiliently biased material configured to open the jaws in response to a compressive force applied to the handle.

4. The surgical instrument of claim 3, wherein the handle comprises a continuous metal or alloy wire connector that forms the arm portions and the leg portions of the handle, wherein first and second legs are non-parallel.

5. The surgical instrument of claim 3, wherein the wire connector comprises an alignment guide formed by at least one of a bent portion of an intermediate portion of the wire connector, and a bend in the first leg of the wire connector that forms an elongated alignment channel through which the second leg extends to maintain the aligned orientation of the first and second clamping surfaces.

6. The surgical instrument of claim 1, wherein the first and second clamping surfaces are arcuate.

7. The surgical instrument of claim 1, wherein the first clamping surface and the second clamping surface form an aperture therebetween when disposed adjacent one another, the aperture extending from the superior surface to the inferior surface.

8. The surgical instrument of claim 1, wherein the inferior surface is curved to conform to the shape of an anatomic structure to be clamped.

9. A method of closing a wound with the instrument of claim 1, comprising:

moving the handle to overcome the resilient bias and open the clamp;

placing the clamp on the wound with margins of the wound between clamping surfaces of the first and second jaws;

closing the jaws of the clamp with the margins of the wound retained between the clamping surfaces.

10. The method of claim 9, wherein the instrument comprises a guide slot extending transversely through the first and second jaws to define a needle trajectory, and the method further comprises introducing a curved needle in the needle trajectory and placing a suture across the margins of the wound along the needle trajectory.

11. The method of claim 9, wherein the compression prongs comprise barbs, and the method further comprises inserting the barbs into the skin as the jaws of the clamp close with the margins of the wound retained between the clamping surfaces.

12. The method of claim 9, wherein the wound is a surgical incision.

13. The method of claim 12, wherein the surgical incision is opened and closed multiple times during a surgical procedure by removing and reapplying the clamp to the incision.

14. The method of claim 12, wherein the surgical incision is a sclerotomy incision in an eye, and choroid underlying the sclerotomy incision is pre-treated with a laser to cauterize blood vessels in the choroid underlying the sclerotomy incision prior to making the sclerotomy incision.

15. The method of claim 12, wherein the surgical incision is a sclerotomy incision in an eye of a recipient, and retinal tissue or artificial retina is transplanted into the retina of the eye of the recipient, further comprising;

immunosuppressing the recipient of the retinal tissue or artificial retina following the procedure to minimize rejection of the transplanted retinal tissue or artificial retina.

16. A surgical instrument for clamping a target structure, comprising:

a clamp having a first jaw forming a first clamping surface, and a second jaw forming a second clamping surface that opposes the first clamping surface, the clamping surfaces including an inferior surface of the clamp cooperatively formed by the first and second jaws for resting on tissue to be clamped;

a handle connecting the first and second jaws wherein the handle has a resilient bias that resiliently biases the first clamping surface and second clamping surface against each other into a substantially closed relationship for clamping the target structure;

wherein the handle is movable to overcome the resilient bias and open the clamp by moving the first jaw and/or the second jaw to an open position while maintaining the first clamping surface and the second clamping surface in a substantially aligned orientation relative to one another; and a suture guide slot that extends through the first and second jaws to define a needle trajectory for placing a suture across an incision that is closed by the clamp, a clamp thickness tapering toward the clamping surfaces and the suture guide slot to minimize clamp thickness along the needle trajectory, the suture guide slot being an elongated opening that extends transversely through the first and second jaws a predetermined distance that corresponds to entrance and exit points of the suture placed across the incision.

17. The surgical instrument of claim 16, wherein the guide slot comprises a bevel at its ends to guide a needle along the needle trajectory.

18. The surgical instrument of claim 16, wherein the superior surface is arcuate and tapers symmetric with respect to the opposing clamping surfaces, and the suture guide slot extends substantially perpendicularly to the opposing clamping surfaces.

19. The surgical instrument of claim 16, wherein the clamp further comprises compression prongs that extend downwardly from the inferior surface of each jaw and are configured to extend toward the incision to be closed.

20. The surgical instrument of claim 16, wherein the first and second jaws include a superior surface opposite the inferior surface, the first clamping surface and the second clamping surface forming an aperture therebetween when disposed adjacent one another, the aperture extending from the superior surface to the inferior surface.

21. A surgical instrument for clamping a target structure, comprising:

a clamp having a first jaw forming a first clamping surface, and a second jaw forming a second clamping surface that opposes the first clamping surface, the clamping surfaces including an inferior surface of the clamp cooperatively formed by the first and second jaws for resting on tissue to be clamped, the first and second jaws including a superior surface opposite the inferior surface, the first clamping surface and the second clamping surface forming an aperture therebetween when disposed adjacent one another, the aperture extending from the superior surface to the inferior surface;

a handle connecting the first and second jaws wherein the handle has a resilient bias that resiliently biases the first clamping surface and second clamping surface against each other into a substantially closed relationship for clamping the target structure;

wherein the handle is movable to overcome the resilient bias and open the clamp by moving at least one of the first jaw and the second jaw to an open position while maintaining the first clamping surface and the second clamping surface in a substantially aligned orientation relative to one another, the handle including an arm portion and a leg portion, wherein the arm portion comprises first and second arms that are respectively connected to the first jaw and the second jaw, and the leg portion comprises first and second legs that join at a common apex of the leg portion with a resilient bias that resiliently biases the first clamping surface and second clamping surface against each other into a substantially closed relationship for clamping the target structure.

22. The surgical instrument of claim 21, wherein the aperture is substantially round.

23. The surgical instrument of claim 21, wherein the first clamping surface includes a first clamping surface recess, and the second clamping surface includes a second clamping surface recess, the first and second clamping surface recesses forming the aperture when the first and second clamping surfaces are disposed adjacent one another.

24. The surgical instrument of claim 21, wherein the clamp further comprises compression prongs that extend downwardly from the inferior surface of each jaw for extending toward an incision to be closed.

25. The surgical instrument of claim 21, wherein the first and second legs are disposed in a plane that extends at an angle to the first and second jaws of the clamp.

26. The surgical instrument of claim 21, wherein the first and second arms are substantially parallel.

* * * * *